United States Patent [19]

Pascal et al.

[11] Patent Number: 5,010,075
[45] Date of Patent: Apr. 23, 1991

[54] SUBSTITUTED IMIDAZOLYL-ALKYL-PIPERAZINE AND -DIAZEPINE DERIVATIVES

[75] Inventors: Jean C. Pascal, Cachan, France; Chi-Ho Lee, Palo Alto, Calif.; Brian J. Alps, Linlithgow, Scotland; Henri Pinhas, Paris, France; Roger L. Whiting, Los Altos, Calif.

[73] Assignee: Syntex Pharmaceuticals Ltd., Berkshire, England

[21] Appl. No.: 505,379

[22] Filed: Apr. 6, 1990

Related U.S. Application Data

[62] Division of Ser. No. 313,656, Feb. 21, 1989, Pat. No. 4,935,417, which is a division of Ser. No. 42,181, Apr. 24, 1987, Pat. No. 4,829,065.

[51] Int. Cl.$^5$ .................. C07D 243/08; C07D 403/06; A61K 31/55
[52] U.S. Cl. .................... 514/218; 514/252; 540/575; 540/603; 544/370
[58] Field of Search ................. 540/603, 575; 514/218

[56] References Cited

U.S. PATENT DOCUMENTS

| | | | |
|---|---|---|---|
| 3,362,956 | 1/1968 | Archer | 260/268 |
| 3,491,098 | 1/1970 | Archer | 260/268 |
| 3,631,043 | 12/1971 | Regnier et al. | 260/250 A |
| 3,649,631 | 3/1972 | Koppe et al. | 260/268 H |
| 3,927,011 | 12/1975 | Nakanishi et al. | 260/296 R |
| 4,022,783 | 5/1977 | Shroff et al. | 260/268 H |
| 4,243,806 | 1/1981 | Raeymaekers et al. | 544/396 |
| 4,404,382 | 9/1983 | Gall | 544/360 |

FOREIGN PATENT DOCUMENTS

| | | |
|---|---|---|
| 0054974 | 5/1982 | European Pat. Off. . |
| 0072623 | 4/1983 | European Pat. Off. . |
| 1551993 | 9/1979 | United Kingdom . |
| 2022073 | 12/1979 | United Kingdom . |
| 2097790 | 11/1982 | United Kingdom ................ 514/218 |

Primary Examiner—Mukund J. Shah
Assistant Examiner—Philip I. Dalton
Attorney, Agent, or Firm—David A. Lowin; Tom M. Moran

[57] ABSTRACT

Substituted imidazolyl-alkyl-piperazine and diazepine derivatives of Formula A:

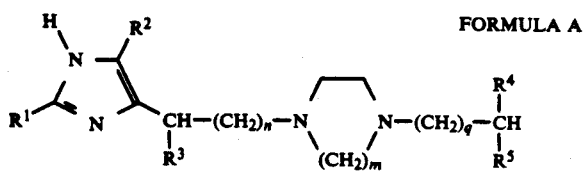

FORMULA A wherein:
$R^1$ is aryl, lower alkyl, cycloalkyl or hydrogen;
$R^2$ is aryl, lower alkyl or hydrogen;
$R^3$ is lower alkyl, hydroxy, or hydrogen;
$R^4$ is aryl or hydrogen;
$R^5$ is aryl or hydrogen;
m is two or three;
n is zero, one or two, provided that when $R^3$ is hydroxy, n is one or two; and
q is zero, one, two, or three;

and the pharmaceutically acceptable salts thereof, are calcium channel antagonists useful for treating mammals having a variety of disease states, such as stroke, epilepsy, hypertension, angina, migraine, arrhythmia, thrombosis, embolism and also for treatment of spinal injuries.

13 Claims, No Drawings

SUBSTITUTED IMIDAZOLYL-ALKYL-PIPERAZINE AND -DIAZEPINE DERIVATIVES

This is a division of application Ser. No. 313,656, filed Feb. 21, 1989, now U.S. Pat. No. 4,935,417; which is a division of application Ser. No. 042,181, filed Apr. 24, 1987, now U.S. Pat. No. 4,829,065, both incorporated herein by reference.

BACKGROUND OF THE INVENTION

1. Field of the Invention

This invention relates to substituted imidazolyl-alkyl-piperazine and diazepine derivatives, the pharmaceutically acceptable salts thereof, methods of making these compounds, and pharmaceutical compositions containing these compounds. The compounds of this invention are calcium entry blockers having selectivity for cerebral blood vessels, and have protective activity against some of the deleterious effects resultant upon cerebral ischemia. The compounds of this invention are, therefore, useful for treating mammals having a variety of disease states, such as stroke, epilepsy, hypertension, angina, migraine, arrhythmia, thrombosis, embolism and also for treatment of spinal injuries.

2. Background Information and Related Art

Substituted piperazines have been described as having a variety of pharmaceutical activities.

For example, U.S. Pat. No. 3,362,956 and its cip U.S. Pat. No. 3,491,098, disclose a series of substituted piperazines to be useful as tranquilizers, sedatives, adrenolytic agents, hypothermic agents, anti-convulsants, hypotensive agents and cardiovascular agents. For example, in the U.S. Pat. No. '956 patent, each atom of the piperazine ring could be substituted with a plurality of radicals, for example, the 1-position with lower alkyl, benzhydryl, phenyl-lower-alkyl or phenyl-lower-alkenyl (optionally substituted on the benzene ring), among other substituents. The piperazine includes a lower alkylene (1 to 6 carbons) chain at the 4-position with an optionally-substituted heterocyclic ring at the end. Among the heterocyclic rings encompassed by the '956 disclosure is a 4(5)-imidazolyl radical. The heterocyclic ring in the '098 patent is limited the 4(5)-imidazolyl radical, but no substitutions are disclosed.

Compounds having selective vascular relaxant activity, such as those of the present invention, have remained desired.

SUMMARY OF THE INVENTION

A first aspect of this invention encompasses compounds having the structures represented by Formula A:

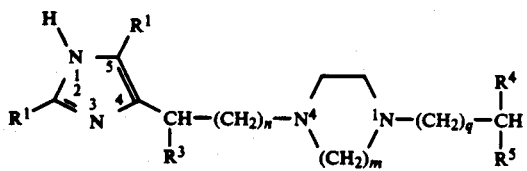

FORMULA A wherein:
R$^1$ is aryl, lower alkyl, cycloalkyl or hydrogen;
R$^2$ is aryl, lower alkyl or hydrogen;
R$^3$ is lower alkyl, hydroxy, or hydrogen;
R$^4$ is aryl or hydrogen;
R$^5$ is aryl or hydrogen;
m is two or three;
n is zero, one or two, provided that when R$^3$ is hydroxy, n is one or two; and
q is zero, one, two, or three;
and the pharmaceutically acceptable salts thereof.

A further aspect of the present invention encompasses methods of making compounds of Formula A, as hereinafter described.

A still further aspect of the present invention encompasses methods of treating a mammals having a variety of disease states, such as stroke, epilepsy, hypertension, angina, migraine, arrhythmia, thrombosis, embolism and also for treatment of spinal injuries, comprising administering a therapeutically effective amount of compound of Formula A to a mammal.

Another aspect of the present invention encompasses pharmaceutical formulations comprising a compound of Formula A and a pharmaceutically acceptable excipient.

DETAILED DESCRIPTION OF THE INVENTION

Definitions

The numbering of the piperazines and diazepines of the present invention is as follows:

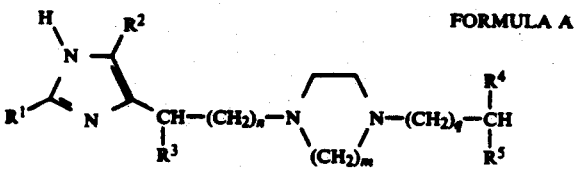

The compounds of the invention will be named using the above-shown numbering system as 1-[optionally mono- or di-aryl]-alkyl-4-[(optionally 2- and/or 5-substituted-imidazolyl)-optionally-substituted-alkyl]-piperazines and -diazepines. Some representative compounds are named as follows:

the compound of Formula A where R$^1$ is 4-methylphenyl, R$^2$ is methyl, R$^3$ is hydrogen, R$^4$ is phenyl, R$^5$ is phenyl, m is 2, n is 0 and q is 0, is named "1-diphenylmethyl-4-[(2-(4-methylphenyl)-5-methyl-1H-imidazol-4-yl)methyl]piperazine";

the compound of Formula A where R$^1$ is 4-methylphenyl, R$^2$ is hydrogen, R$^3$ is hydrogen, R$^4$ is phenyl, R$^5$ is phenyl, m is 2, n is 0 and q is 0, is named "1-diphenylmethyl-4-[(2-(4-methylphenyl)-1H-imidazol-4-yl)methyl]piperazine";

the compound of Formula A where R$^1$ is phenyl, R$^2$ is methyl, R$^3$ is methyl, R$^4$ is phenyl, R$^5$ is phenyl, m is 2, n is 0 and q is 0, is named "1-diphenylmethyl-4-[1-(2-phenyl-5-methyl-1H-imidazol-4-yl)ethyl]piperazine";

the compound of Formula A where R$^1$ is cyclohexyl, R$^2$ is methyl, R$^3$ is ethyl, R$^4$ is phenyl, R$^5$ is 2,3-dimethoxyphenyl, m is 2, n is 2 and q is 2, is named "1-[3-phenyl-3-(2,3-dimethoxyphenyl)propyl]-4-[3-(2-cyclohexyl-5-methyl-1H-imidazol-4-yl)pentyl]piperazine";

the compound of Formula A where R$^1$ is phenyl, R$^2$ is methyl, R$^3$ is hydroxy, R$^4$ is phenyl, R$^5$ is phenyl, m is 2, n is 1 and q is 0, is named "1-diphenylmethyl-4-[2-(2-phenyl-5-methyl-1H-imidazol-4-yl)-2-hydroxyethyl]piperazine";

the compound of Formula A where $R^1$ is phenyl, $R^2$ is methyl, $R^3$ is hydrogen, $R^4$ is 4-fluorophenyl, $R^5$ is 4-fluorophenyl, m is 2, n is 0 and q is 3, is named "1-[4,4-di-(4-fluorophenyl)butyl]-4-[(2-phenyl-5-methyl-1H-imidazol-4-yl)methyl]piperazine"; and the compound of Formula A where $R^1$ is 2,4-dihydroxyphenyl, $R^2$ is methyl, $R^3$ is hydrogen, $R^4$ is phenyl, $R^5$ is phenyl, m is 3, n is 0 and q is 0, is named "1-diphenylmethyl-4-[(2-(2,4-dihydroxyphenyl)-5-methyl-1H-imidazol-4-yl)methyl]diazepine".

Compounds of the invention where $R^3$ is lower alkyl or hydroxy, and/or where $R^4$ and $R^5$ are different and neither is hydrogen will have one or two chiral centers and may display optical activity. The optical isomers may be separated using conventinal methods. For purposes of the present invention, any compound having optical activity shall include each individual isomer as well as mixtures thereof.

As used herein, the term "alkyl" means a branched or unbranched saturated hydrocarbon radical having from 1-6 carbon atoms. Examples include methyl, ethyl, propyl, t-butyl, n-pentyl and n-hexyl, and the like.

As used herein, the term "cycloalkyl" means a saturated carbocyclic hydrocarbyl ring having from 3 to 7 ring carbon atoms, one of which has a single available valence. Examples include cyclopropyl, cyclopentyl, cyclohexyl, and the like.

As used herein, the term "alkoxy" means the group —OR wherein R is alkyl as defined above. Examples include methoxy, ethoxy, propoxy, t-butoxy, n-pentyloxy, n-hexyloxy, and the like.

As used herein, the term "lower" modifies alkyl and alkoxy and refers to those radicals having four carbon atoms or less.

As used herein, the term "halo" means fluoro, chloro, bromo and/or iodo.

As used herein, the term "aryl" refers to phenyl and optionally mono-, di-, and tri-substituted phenyl, wherein the optional substituents are lower alkyl, lower alkoxy, hydroxy, trifluoromethyl, or halo. Examples include 2-chlorophenyl, 2-trifluoromethylphenyl, 4-methoxyphenyl, 4-chlorophenyl, 3,4-dimethoxyphenyl, 4-hydroxyphenyl, 4-methylphenyl, 3-t-butylphenyl, 4-hexylphenyl, and the like.

As used herein, the term "treatment" or "treating" means any treatment of a disease in a mammal, and includes:

(i) preventing the disease, i.e., causing the clinical symptoms of the disease not to develop;

(ii) inhibiting the disease, i.e., arresting the development of clinical symptoms; and/or (iii) relieving the disease, i.e., causing the regression of clinical symptoms.

As used herein, the terms "pharmaceutically acceptable salts" refers to those salts that retain biological effectiveness and properties of the neutral parent compounds and which are not biologically or otherwise undesirable. Pharmaceutically acceptable acid addition salts may be formed with inorganic acids, such as hydrochloric acid, hydrobromic acid, sulfuric acid, nitric acid, phosphoric acid, and the like, and with organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, para-toluenesulfonic acid, salicylic acid, and the like. The salts may be single or multiple salts of one or more anions, e.g., from the above-described acids.

PRESENTLY PREFERRED EMBODIMENTS

Presently preferred embodiments of this invention are compounds of Formula A wherein $R^1$ is aryl; further preferred are the compounds where $R^1$ is aryl, m is 2; q is 0; n is 0; $R^2$ is methyl; and $R^3$ is hydrogen. The phramaceutically acceptable salts of these compounds are also preferred, especially the mono-, di- and tri-hydrochlorides.

Particularly preferred are those compounds where $R^1$ is 4-methylphenyl or phenyl and $R^4$ and $R^5$ are the same, e.g., both phenyl, i.e., 1-(diphenylmethyl)-4-[(2-(4-methylphenyl)-5-methyl-1H-imidazol-4-yl)methyl]piperazine and 1-(diphenylmethyl)-4-[(2-phenyl-5-methyl-1H-imidazol-4-yl)methyl]piperazine and the trihydrochloride salts thereof.

Other preferred compounds include those where $R^1$ is aryl or cycloalkyl; especially those where $R^3$ is lower alkyl, particularly methyl and isopropyl; m is 2; q is 0; n is 0; and $R^1$, $R^4$ and $R^5$ are all phenyl.

Still other preferred compounds include those where q is 3; n is 0; $R^1$ is phenyl; $R^3$ hydrogen; and $R^4$ and $R^5$ are both 4-fluorophenyl.

Another preferred compound is that wherein m is 3; q is 0; n is 0; $R^1$ is phenyl; $R^2$ is methyl; $R^3$ is hydrogen; and $R^4$ and $R^5$ are both phenyl.

UTILITY AND METHODS OF ADMINISTRATION

General Utility

The compounds of this invention are useful for treating mammals having a variety of vascular disease states, and have protective activity against some of the deleterious effects resultant upon cerebral ischemia. Disease states that may be treated include stroke, migraine, epilepsy, hypertension, angina, arrhythmia, thrombosis, and embolism. The compounds of this invention are also useful for treating spinal injuries, and are particularly useful for treating cerebrovascular disease states, for example, stroke.

Generally, vascular disease states are found in mammals, including: domestic commercial animals such as horses, cattle, sheep and pigs; domestic house animals such as dogs, cats, and the like; and particularly humans.

Activity Testing

Activity for treating vascular disease states can be determined in vitro by determining selective vascular relaxant activity, and in vivo by determining general cardiovascular activity.

In vitro calcium antagonistic activity of the compounds of this invention is determined by an assay using rat aortic strip, which is a modification of that described by R. Kent, et al., *Federation Proceedings*, 40, 724 (1981). Cerebrovascular selectivity of action is determined by comparing potencies on rabbit basilar artery and rabbit ear artery using a modification of the procedure described by R. Towart, et al., *Arzneim. Forsh.*, 32(I), 338-346 (1982).

In vivo protective effects of the compounds of this invention against the deleterious effects of cerebral ischemia are determined by use of the standard gerbil brain ischemia model. This assay is a modification of that described by T. Kirino, *Brain Res.*, 239, 57–69P (1982).

General Administration

The compounds of this invention are administered at a therapeutically effective dosage, i.e., a dosage sufficient to provide treatment for the disease states previously described. Administration of the active compounds and salts described herein can be via any of the accepted modes of administration for agents that serve similar utilities.

Generally, a daily dose of from 0.02 to 50 mg/kg of body weight per day of the active compound of Formula I. Most conditions respond to treatment comprising a dosage level on the order of 0.1 to 4 mg/kilogram of body weight per day. Thus, for administration to a 70 kg person, the dosage range would be about 1.4 to 3500 mg per day, preferably about 7.0 to 280 mg per day.

Depending on the specific disease state, administration can be via any accepted systemic route, for example, via parenteral, oral, intravenous, or nasal routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical carrier or excipient and an active compound of Formula A and, in addition, may include other medicinal agents, pharmaceutical agents, carriers, adjuvants, etc.

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of this invention are generally administered as a pharmaceutical composition which comprises a pharmaceutical excipient in combination with a compound of Formula A. The level of the drug in a formulation can vary within the full range employed by those skilled in the art, e.g., from about 0.01 percent weight (% w) to about 99.99% w of the drug based on the total formulation and about 0.01% w to 99.99% w excipient. Preferably, the formulation will be about 3.5 to 60% by weight of the pharmaceutically active compound, with the rest being suitable pharmaceutical excipients.

Oral Administration

The preferred manner of administration, for the conditions detailed above, is oral using a convenient daily dosage regimen which can be adjusted according to the degree of affliction. For such oral administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions may contain between 0.01 wt/% and 99.99 wt/% of the compound of Formula A, but preferably such compositions will contain between 25 wt/% and about 80 wt/%.

Preferably the compositions will take the form of a pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like.

Suppositories

For systemic administration via suppository, traditional binders and carriers include, for example, polyalkaline glycol or triglycerides [e.g., PEG 1000 (96%) and PEG 4000 (4%)]. Such suppositories may be formed from mixtures containing active ingredients in the range of from about 0.5 wt/% to about 10 wt/%; preferably from about 1 wt/% to about 2 wt/%.

Liquids

Liquid pharmaceutically administerable compositions can, for example, be prepared by dissolving, dispersing, etc. an active compound (about 0.5% to about 20%), as described above, and optional pharmaceutical adjuvants in a carrier, such as, for example, water, saline, aqueous dextrose, glycerol, ethanol and the like, to thereby form a solution or suspension.

Actual methods of preparing such dosage forms are known, or will be apparent, to those skilled in this art; for example, see *Remington's Pharmaceutical Sciences*, Mack Publishing Company, Easton, Pa., 16th Ed., 1980. The composition to be administered will, in any event, contain a quantity of the active compound(s) in a pharmaceutically effective amount for relief of the particular condition being treated in accordance with the teachings of this invention.

Methods of Preparation

The compounds of this invention can be made as shown in Reaction Schemes I–V, wherein $R^1$, $R^2$, $R^3$, $R^4$, and $R^5$ have the same meaning as set forth above in the Summary Of The Invention, newly introduced variable $R^6$ is lower alkyl, and X is halo.

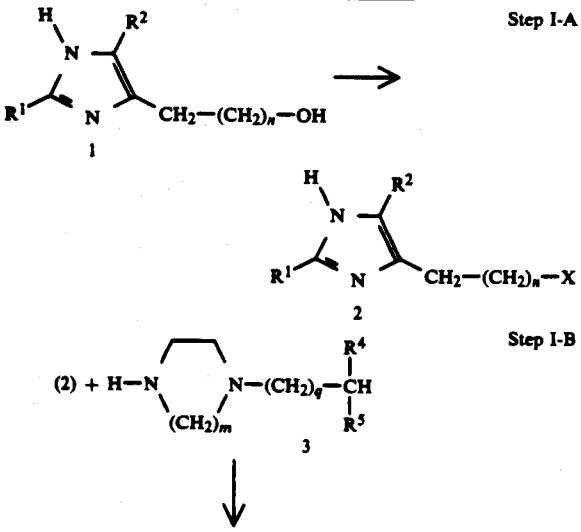

-continued
REACTION SCHEME I

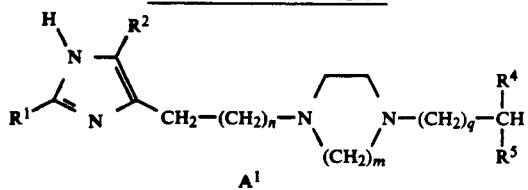

I. Preparation of Formula A Where $R^3$ is Hydrogen

Referring to Reaction Scheme I, in Step I-A a mixture of a compound of Formula 1 with an inert hydrocarbon solvent (for example, benzene, toluene and the like) is contacted with a slight excess of a halogenating agent, for example, a thionyl halide (such as thionyl chloride), to produce the corresponding alkyl halide derivative, compound of Formula 2. Compounds of Formula 1 are obtained using the procedures of Dziuron and Sunack [Arch. Pharm., 306, 347 (1973), Arch. Pharm., 307, 46 (1973) and Bull. Soc. Chim. France, (1971), 1052] and Cornforth and Huang, J. Chem. Soc., (1948) 731-735. The reaction is conducted at a temperature from about 0° C. to the reflux temperature of the solvent, but preferably between about 40° C. and 65° C.

In Step I-B, the compound of Formula 2 is contacted with a compound of Formula 3 in a condensation reaction, for example, at a temperature from about 25°-80° C., preferably at the reflux temperature of the solvent system used.

The 1-substituted piperazines of Formula 3 are commercially available or can be made by the procedures of Hamlin, et al., J. Am. Chem. Soc., 71, 31 (1949) or Cheeseman, J. Chem Soc., (1975), 115-123. Diazepine analogs (i.e., those compounds where m is 3) can be made by this method using diazepine as the starting material instead of piperazine. An alkaline solution is made by dissolving a compound of Formula 3 in a polar solvent (for example, ethanol and water, methanol and water, or a mixture such as, acetone in water, dimethylformamide in water, isopropanol in water, tetrahydrofuran in water; in the ratio of about 10:90, preferably about 60:40), and adding a base (such as sodium hydroxide, potassium hydroxide, sodium carbonate, sodium bicarbonate, potassium carbonate, potassium bicarbonate, and the like). The alkaline solution is heated to reflux.

A solution of the compound of Formula 2 dissolved in the same polar solvent is added dropwise to the refluxing solution of the compound of Formula 3. After about 1 to 8 hours, preferably about 4 to 5 hours, the condensed product of Formula $A^1$ is precipitated from the reaction mixture. The reaction mixture is allowed to stand at room temperature, for example, for about 8 to 16 hours, or overnight. The resulting crystals are removed by filtration and recrystallized in ethanol giving the free base of Formula $A^1$.

The free base can be converted to the salt by dissolving the free base in a suitable organic solvent, such as ethanol or ether, and extracting with acidic aqueous solution. The use of heat may be required to dissolve the free base, depending upon the acid chosen.

The salt can be converted back to the free base by suspending it, for example in ether, and adding an excess of a dilute aqueous base, such as potassium carbonate, until the salt dissolves. The organic layer is separated, washed with water, dried and evaporated to yield the free base.

REACTION SCHEME II

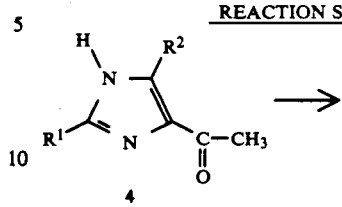
Step II-A

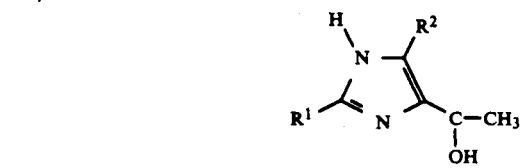

Step II-B

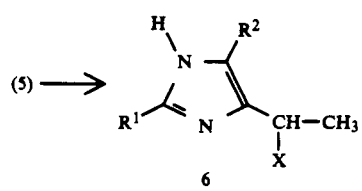

(6) + (3) ⟶
Step II-C

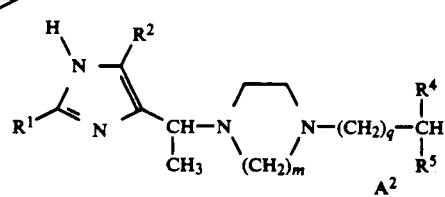

II. Preparation of Formula A Where $R^3$ is Methyl and n is 0

Referring to Reaction Scheme II, in Step II-A a compound of Formula 4 [obtained using the procedure of Vecchio, et al., Chim. Ind. (Milan), 58(6), 451 (1976) or of Haruki, et al., Zasshiu, 86(9), 942-946 (1965) (Japan)] is reduced by contacting it with a reducing agent, such as a hydride (for example, potassium borohydride, or lithium aluminum hydride) in an alcoholic solution (for example, methanol, ethanol, isopropanol, and the like). The solution is stirred for about 8 to 16 hours, e.g., overnight, and the resulting solid material, of Formula 5, is removed by filtration, washed, dried and used in the next step without further purification.

In Step II-B, the crude compound of Formula 5 is dissolved in an inert solvent (for example, chloroform, dichloromethane, benzene, toluene, and the like). A halogenating agent, such as thionyl chloride, is added to the solution and the resulting mixture is heated at reflux for a period of time between 1 and 10 hours, preferably between about 4 and 6 hours. After cooling, the solvent is removed under reduced pressure and the residue is triturated in acetone to give a compound of Formula 6.

In Step II-C, the compound of Formula 6 and a compound of Formula 3 are reacted together under the conditions described in Step I-B to give a compound according to Formula $A^2$. An oil product may be separated, dissolved in ether, and acidified to precipitate. The reaction time is about 1 to 24 hours, preferably about 4 to 5 hours.

REACTION SCHEME III

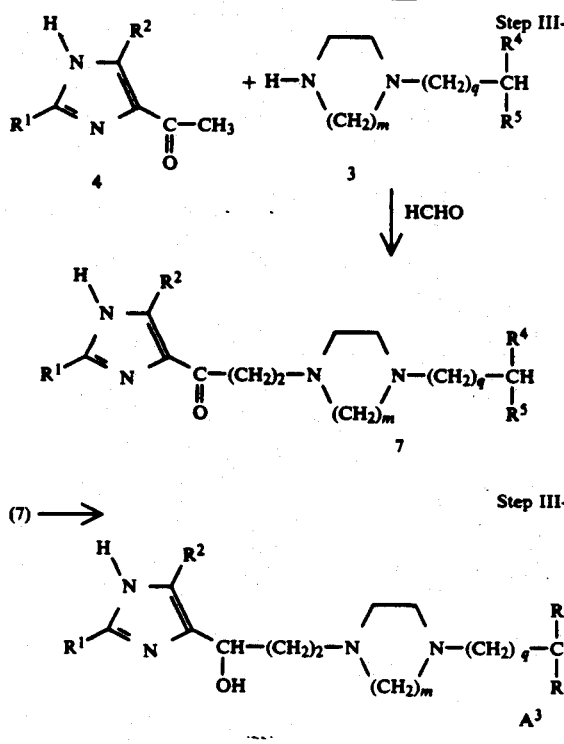

III. Preparation of Formula A Where $R^3$ is Hydroxyl and n is 2

Referring to Reaction Scheme III, in Step III-A a methyl ketone, such as a compound of Formula 4, an amine, such as a compound of Formula 3, and formaldehyde are reacted together under the conditions typically used for a Mannich reaction, to give a compound of Formula 7.

In Step III-B, the compound of Formula 7 is reduced under conditions similar to those described in Step II-A, to give a compound of Formula $A^3$.

REACTION SCHEME IV

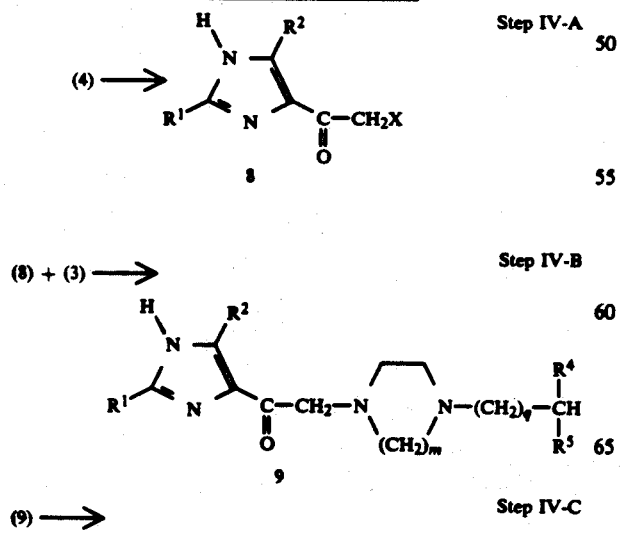

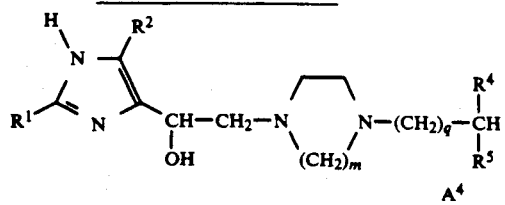

IV. Preparation of Formula A Where $R^3$ is Hydroxyl and n is 1

Referring to Reaction Scheme IV, in Step IV-A a compound of Formula 4 is halogenated, by contacting it with a halogenating agent, for example, thionyl halide, under conditions similar to those described in Step I-A, to give a compound of the Formula 8.

In Step IV-B, a compound of Formula 8 and a compound of Formula 3 are condensed by contacting them under conditions similar to those described for Step I-B, to give a compound of Formula 9.

In Step IV-C, a compound of Formula 9 is reduced, by contacting it with a reducing agent under conditions similar to those described for Step III-A to give a compound of Formula $A^4$.

REACTION SCHEME V

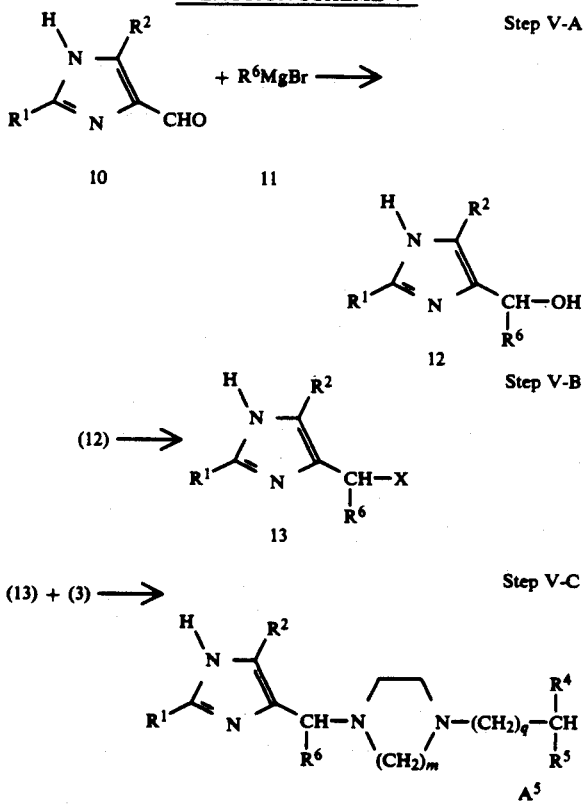

V. Preparation of Formula A Where $R^3$ is Lower Alkyl

Referring to Reaction Scheme V, in Step V-A, the Grignard reagent of a lower alkyl halide, the compound of Formula 11, is contacted with an imidazole compound of Formula 10 [obtained using the procedure of Cornforth and Huang, *J. Chem. Soc.*, (1948), 731–735] in a neutral solvent (for example, diethyl ether, tetrahydrofuran, tetrahydropyran, and the like) and refluxed for between 15 minutes and 2 hours, preferably between 20 minutes and 40 minutes, and is then cooled and poured into ice water. The aqueous layer is extracted with a suitable organic solvent, such as diethyl ether. When the solvent is removed under reduced pressure, a residue is formed that can be recrystallized in ethanol yielding a compound of Formula 12.

In Step V-B, a compound of Formula 12 is halogenated under conditions similar to those described for Step I-A, to give a compound of Formula 13.

In Step V-C, a compound of Formula 13 and a compound of Formula 3 are contacted under conditions similar to those described for Step I-B, to give a compound of Formula $A^5$.

Preferred Processes

The compounds of the present invention can be prepared according to the following last steps, in which non-essential substituents are not referenced, but will be apparent from reference to the foregoing reaction schemes:

a 4-haloalkyl-1H-imidazole (or a salt thereof) is condensed with an alkyl-4-piperazine to give a compound according to Formula A where m is 2;

a 4-haloalkyl-1H-imidazole (or a salt thereof) is condensed with an alkyl-4-diazepine to give a compound according to Formula A where m is 3;

a 4-(1-halo-$C_2$-$C_4$-alkyl)-1H-imidazole (or a salt thereof) is condensed with an alkyl-4-piperazine to give a compound according to Formula A where m is 2, and $R^3$ is lower alkyl;

a 4-(1-halo-$C_2$-$C_4$-alkyl)-1H-imidazole (or a salt thereof) is condensed with an alkyl-4-diazepine to give a compound according to Formula A where m is 3, and $R^3$ is lower alkyl;

a 1-alkyl-4-[(1H-imidazol-4-yl)-1-oxo-alkyl]piperazine is reduced to give the corresponding compound according to Formula A where m is 2, and $R^3$ is hydroxy;

a 1-alkyl-4-[(1H-imidazol-4-yl)-1-oxo-alkyl]diazepine is reduced to give the corresponding compound according to Formula A where m is 3, and $R^3$ is hydroxy;

exemplifying the preparation of a further substituted compound, a 2-(aryl)-4-($\omega$-haloalkyl)-5-alkyl-1H-imidazole (or a salt thereof) is condensed with a diarylalkyl-4-piperazine to give a compound according to Formula A where $R^1$ is aryl, $R^2$ is alkyl, $R^3$ is hydrogen, $R^4$ and $R^5$ are aryl, m is 2, n is 0–2, and q is 0–3;

contacting a pharmaceutically acceptable acid with a compound of Formula A to form the corresponding acid addition salt of Formula A;

substituting a pharmaceutically acceptable acid salt of Formula A with another pharmaceutically acceptable acid; and contacting an acid addition salt of Formula A with a base to form the corresponding free base compounds of Formula A.

EXAMPLES

The following examples are given to enable those skilled in the art to more clearly understand and to practice the present invention. They should not be considered as a limitation on the scope of the invention, but merely as being illustrative and representative thereof.

EXAMPLE 1

1-Diphenylmethyl-4-[(2-(4-methylphenyl)-5-methyl-1H-imidazol-4-yl)methyl]piperazine and Derivatives Thereof 1A. Formula A Where $R^1$ is 4-Methylphenyl; $R^2$ is Methyl; $R^3$ is Hydrogen; $R^4$ and $R^5$ are Phenyl; m is 2; n is 0; and q is 0

50 Grams (0.2 mol) of 2-(4-methylphenyl)-4-chloromethyl-5-methyl-1H-imidazole hydrochloride dissolved in 200 ml of a mixture of ethanol:water 6:4 were added dropwise to a refluxing solution of 55 grams (0.2 mol) of N-(diphenylmethyl)piperazine and 24 grams (0.6 mol) sodium hydroxide in 200 ml of a mixture of ethanol:water 6:4. After 2 to 3 hours 1-diphenylmethyl-4-[(2-(4-methylphenyl)-5-methyl-1H-imidazol-4-yl)methyl]piperazine precipitated from the reaction mixture. After having left the crystals standing at room temperature, they were removed by filtration and recrystallized from methanol to give the free base which melted at 220°–222° C.

1B. Formula A Varying $R^1$ and $R^2$

Similarly, following the procedure of Part A above, but replacing 2-(4-methylphenyl)-4-chloromethyl-5-methyl-1H-imidazole hydrochloride with:

2-phenyl-4-chloromethyl-5-methyl-1H-imidazole hydrochloride;

2-methyl-4-chloromethyl-5-methyl-1H-imidazole hydrochloride;

2-t-butyl-4-chloromethyl-5-methyl-1H-imidazole hydrochloride;

2-(3-methylphenyl)-4-chloromethyl-5-methyl-1H-imidazole hydrochloride;

2-(2-methylphenyl)-4-chloromethyl-5-methyl-1H-imidazole hydrochloride;

2-(4-t-butylphenyl)-4-chloromethyl-5-methyl-1H-imidazole hydrochloride;

2-(3-t-butylphenyl)-4-chloromethyl-5-methyl-1H-imidazole hydrochloride;

2-(2-t-butylphenyl)-4-chloromethyl-5-methyl-1H-imidazole hydrochloride;

2-(4-chlorophenyl)-4-chloromethyl-5-methyl-1H-imidazole hydrochloride;

2-(3-chlorophenyl)-4-chloromethyl-5-methyl-1H-imidazole hydrochloride;

2-(2-chlorophenyl)-4-chloromethyl-5-methyl-1H-imidazole hydrochloride;

2-(4-methoxyphenyl)-4-chloromethyl-5-methyl-1H-imidazole hydrochloride;

2-(3-methoxyphenyl)-4-chloromethyl-5-methyl-1H-imidazole hydrochloride;

2-(2-methoxyphenyl)-4-chloromethyl-5-methyl-1H-imidazole hydrochloride;

2-(2-methylphenyl)-4-chloromethyl-5-ethyl-1H-imidazole hydrochloride;

2-(4-methylphenyl)-4-chloromethyl-5-t-butyl-1H-imidazole hydrochloride;

2-(4-methylphenyl)-4-chloromethyl-1H-imidazole hydrochloride;

2-(3,4-dimethoxyphenyl)-4-bromomethyl-5-methyl-1H-imidazole hydrochloride;

2,5-di-(4-methylphenyl)-4-chloromethyl-1H-imidazole hydrochloride;

2-(cyclopropyl)-4-chloromethyl-5-methyl-1H-imidazole hydrochloride;

4-chloromethyl-5-methyl-1H-imidazole hydrochloride; and 4-chloromethyl-5-(3-methoxyphenyl)-1H-imidazole hydrochloride, there is obtained:

1-diphenylmethyl-4-[(2-phenyl-5-methyl-1H-imidazol-4-yl)methyl]piperazine, the trihydrochloride salt of which has a melting point of 214° C.;
1-diphenylmethyl-4-[(2,5-dimethyl-1H-imidazol-4-yl)methyl]piperazine, the trihydrochloride salt of which has a melting point of about 225° C.;
1-diphenylmethyl-4-[(2-t-butyl-5-methyl-1H-imidazol-4-yl)methyl]piperazine;
1-diphenylmethyl-4-[(2-(3-methylphenyl)-5-methyl-1H-imidazol-4-yl)methyl]piperazine;
1-diphenylmethyl-4-[(2-(2-methylphenyl)-5-methyl-1H-imidazol-4-yl)methyl]piperazine;
1-diphenylmethyl-4-[(2-(4-t-butylphenyl)-5-methyl-1H-imidazol-4-yl)methyl]piperazine;
1-diphenylmethyl-4-[(2-(3-t-butylphenyl)-5-methyl-1H-imidazol-4-yl)methyl]piperazine;
1-diphenylmethyl-4-[(2-(2-t-butylphenyl)-5-methyl-1H-imidazol-4-yl)methyl]piperazine;
1-diphenylmethyl-4-[(2-(4-chlorophenyl)-5-methyl-1H-imidazol-4-yl)methyl]piperazine, the trihydrochloride salt of which has a melting point of 216° C.;
1-diphenylmethyl-4-[(2-(3-chlorophenyl)-5-methyl-1H-imidazol-4-yl)methyl]piperazine, the trihydrochloride salt of which has a melting point of about 215° C.;
1-diphenylmethyl-4-[(2-(2-chlorophenyl)-5-methyl-1H-imidazol-4-yl)methyl]piperazine;
1-diphenylmethyl-4-[(2-(4-methoxyphenyl)-5-methyl-1H-imidazol-4-yl)methyl]piperazine, the trihydrochloride salt of which has a melting point of about 225° C.;
1-diphenylmethyl-4-[(2-(3-methoxyphenyl)-5-methyl-1H-imidazol-4-yl)methyl]piperazine;
1-diphenylmethyl-4-[(2-(2-methoxyphenyl)-5-methyl-1H-imidazol-4-yl)methyl]piperazine;
1-diphenylmethyl-4-[(2-(2-methylphenyl)-5-ethyl-1H-imidazol-4-yl)methyl]piperazine;
1-diphenylmethyl-4-[(2-(4-methylphenyl)-5-t-butyl-1H-imidazol-4-yl)methyl]piperazine;
1-diphenylmethyl-4-[(2-(4-methylphenyl)-1H-imidazol-4-yl)methyl]piperazine;
1-diphenylmethyl-4-[(2-(3,4-dimethoxyphenyl)-5-methyl-1H-imidazol-4-yl)methyl]piperazine, the trihydrochloride salt of which has a melting point of 230° C.;
1-diphenylmethyl-4-[(2,5-di-(4-methylphenyl)-1H-imidazol-4-yl)methyl]piperazine;
1-diphenylmethyl-4-[(2-(cyclopropyl)-5-methyl-1H-imidazol-4-yl)methyl]piperazine;
1-diphenylmethyl-4-[(5-methyl-1H-imidazol-4-yl)methyl]piperazine; and
1-diphenylmethyl-4-[(5-(3-methoxyphenyl)-1H-imidazol-4-yl)methyl]piperazine.

1C. Formula A Varying q, $R^4$ and $R^5$

Similarly, following the procedure of Part A above, but replacing N-(diphenylmethyl)piperazine with:

N-[di-(2-methylphenyl)methyl]piperazine;
N-[di-(3-methylphenyl)methyl]piperazine;
N-[di-(4-methylphenyl)methyl]piperazine;
N-[di-(2-t-butylphenyl)methyl]piperazine;
N-[di-(3-t-butylphenyl)methyl]piperazine;
N-[di-(4-t-butylphenyl)methyl]piperazine;
N-[di-(2-methoxyphenyl)methyl]piperazine;
N-[di-(3-methoxyphenyl)methyl]piperazine;
N-[di-(4-methoxyphenyl)methyl]piperazine;
N-[di-(2-chlorophenyl)methyl]piperazine;
N-[di-(3-chlorophenyl)methyl]piperazine;
N-[di-(4-chlorophenyl)methyl]piperazine;
N-[di-(4-fluorophenyl)methyl]piperazine;
N-benzylpiperazine;
N-[1-(4-chlorophenyl)-1-(phenyl)methyl]piperazine;
N-(2,2-diphenylethyl)piperazine;
N-[3-(phenyl)-3-(4-methoxyphenyl)propyl]piperazine; and
N-(4,4-diphenylbutyl)piperazine, there is obtained:

1-[di-(2-methylphenyl)methyl]-4-[(2-(4-methylphenyl)-5-methyl-1H-imidazol-4-yl)methyl]piperazine;
1-[di-(3-methylphenyl)methyl]-4-[(2-(4-methylphenyl)-5-methyl-1H-imidazol-4-yl)methyl]piperazine;
1-[di-(4-methylphenyl)methyl]-4-[(2-(4-methylphenyl)-5-methyl-1H-imidazol-4-yl)methyl]piperazine;
1-[di-(2-t-butylphenyl)methyl]-4-[(2-(4-methylphenyl)-5-methyl-1H-imidazol-4-yl)methyl]piperazine;
1-[di-(3-t-butylphenyl)methyl]-4-[(2-(4-methylphenyl)-5-methyl-1H-imidazol-4-yl)methyl]piperazine;
1-[di-(4-t-butylphenyl)methyl]-4-[(2-(4-methylphenyl)-5-methyl-1H-imidazol-4-yl)methyl]piperazine;
1-[di-(2-methoxyphenyl)methyl]-4-[(2-(4-methylphenyl)-5-methyl-1H-imidazol-4-yl)methyl]piperazine;
1-[di-(3-methoxyphenyl)methyl]-4-[(2-(4-methylphenyl)-5-methyl-1H-imidazol-4-yl)methyl]piperazine;
1-[di-(4-methoxyphenyl)methyl]-4-[(2-(4-methylphenyl)-5-methyl-1H-imidazol-4-yl)methyl]piperazine;
1-[di-(2-chlorophenyl)methyl]-4-[(2-(4-methylphenyl)-5-methyl-1H-imidazol-4-yl)methyl]piperazine;
1-[di-(3-chlorophenyl)methyl]-4-[(2-(4-methylphenyl)-5-methyl-1H-imidazol-4-yl)methyl]piperazine;
1-[di-(4-chlorophenyl)methyl]-4-[(2-(4-methylphenyl)-5-methyl-1H-imidazol-4-yl)methyl]piperazine, the trihydrochloride salt of which has a melting point of about 225° C.;
1-[di-(4-fluorophenyl)methyl]-4-[(2-(4-methylphenyl)-5-methyl-1H-imidazol-4-yl)methyl]piperazine, the trihydrochloride salt of which has a melting point of about 210° C.;
1-benzyl-4-[(2-(4-methylphenyl)-5-methyl-1H-imidazol-4-yl)methyl]piperazine;
1-[1-(4-chlorophenyl)-1-(phenyl)methyl]-4-[(2-(4-methylphenyl)-5-methyl-1H-imidazol-4-yl)methyl]piperazine;
1-(2,2-diphenylethyl)-4-[(2-(4-methylphenyl)-5-methyl-1H-imidazol-4-yl)methyl]piperazine;
1-[3-(phenyl)-3-(4-methyoxyphenyl)propyl]-4-[(2-(4-methylphenyl)-5-methyl-1H-imidazol-4-yl)methyl]piperazine; and
1-(4,4-diphenylbutyl)-4-[(2-(4-methylphenyl)-5-methyl-1H-imidazol-4-yl)methyl]piperazine.

1D. Formula A Varying $R^1$; $R^2$; $R^4$; $R^5$ and q

Similarly, by following the procedures of Parts B and C above, other compounds of Formula A where $R^3$ is hydrogen, m is 2, and n is 0 are obtained, such as:

1-diphenylmethyl-4-[(2-n-butyl-5-methyl-1H-imidazol-4-yl)methyl]piperazine, the trihydrochloride salt of which has a melting point of about 205° C.;

1-diphenylmethyl-4-[(2-(3-trifluoromethylphenyl)-5-methyl-1H-imidazol-4-yl)methyl]piperazine, the trihydrochloride salt of which has a melting point of about 210° C.;

1-diphenylmethyl-4-[(2-phenyl-1H-imidazol-4-yl)methyl]piperazine, the fumarate salt of which has a melting point of 170° C.;

1-diphenylmethyl-4-[(5-methyl-1H-imidazol-4-yl)methyl]piperazine, the trihydrochloride salt of which has a melting point of about 205° C.;

1-methyl-4-[(2-phenyl-5-methyl-1H-imidazol-4-yl)methyl]piperazine, the trihydrochloride salt of which has a melting point of about 215° C.;

1-di-(4-chlorophenyl)methyl-4-[(2-phenyl-5-methyl-1H-imidazol-4-yl)methyl]piperazine, the trihydrochloride salt of which has a melting point of 220° C.;

1-[4,4-di-(4-fluorophenyl)butyl]-4-[(2-phenyl-5-methyl-1H-imidazol-4-yl)methyl]piperazine, the trihydrochloride salt of which has a melting point of 198° C.; and 1-benzyl-4-[(2-phenyl-5-methyl-1H-imidazol-4-yl)methyl]piperazine, the trihydrochloride salt of which has a melting point of 238° C.

1E. Formula A Varying m

Similarly, by following the procedures of Parts A–D above, but replacing the piperazines there-used with the corresponding diazepines, the compounds of Formula A wherein m is 3 are obtained.

For example, substituting 2-phenyl-4-chloromethyl-5-methyl-1H-imidazole hydrochloride for 2-(4-methylphenyl)-4-chloromethyl-5-methyl-1H-imidazole hydrochloride, and by substituting diphenylmethyl-4-diazepine for diphenylmethyl-4-piperazine, there is obtained 1-diphenylmethyl-4-[(2-phenyl-5-methyl-1H-imidazol-4-yl)methyl]diazepine, the trihydrochloride salt of which has a melting point of about 205° C.

EXAMPLE 2

1-Diphenylmethyl-4-[1-(2-phenyl-5-methyl-1H-imidazol-4-yl)ethyl]piperazine and Derivatives Thereof 2A. Formula 5 Where $R^1$ is Phenyl; and $R^2$ is Methyl 32 Grams (0.59 mol) of potassium borohydride were added portionwise to a solution of 30 g (0.15 mol) of 2-phenyl-4-acetyl-5-methylimidazole in 1500 ml of MeOH. After stirring overnight, a solid material was removed by filtration, then the solvent was evaporated under reduced pressure to give 27 g of 2-phenyl-4-(1-hydroxyethyl)-5-methylimidazole. The crude compound thus isolated was used without further purification.

2B. Formula 6 Where $R^1$ is Phenyl; $R^2$ is Methyl; and X is Chloro

27 Grams (0.13 mol) of 2-phenyl-4-(1-hydroxyethyl)-5-methylimidazole were dissolved in 700 ml of chloroform with 44 ml (0.6 mol) of thionyl chloride and refluxed for 5 hours. After cooling, the mixture was evaporated, the residue triturated in acetone, thereby giving 2-phenyl-4-(1-chloroethyl)-5-methylimidazole hydrochloride, m.p. 190° C.

2C. Formula 6 Varying $R^1$, $R^2$, and the Length of Alkyl at Position 4 of the Imidazole Similarly, following the procedures of Part A and B above, but replacing 2-phenyl-4-acetyl-5-methylimidazole with:

2-(phenyl)-4-(2-methylpropanoyl)-5-methylimidazole;
2-(3-methylphenyl)-4-acetyl-5-methylimidazole;
2-(2-methylphenyl)-4-acetyl-5-methylimidazole;
2-(4-t-butylphenyl)-4-acetyl-5-methylimidazole;
2-(3-t-butylphenyl)-4-acetyl-5-methylimidazole;
2-(2-t-butylphenyl)-4-acetyl-5-methylimidazole;
2-(4-chlorophenyl)-4-acetyl-5-methylimidazole;
2-(3-chlorophenyl)-4-acetyl-5-methylimidazole;
2-(2-chlorophenyl)-4-acetyl-5-methylimidazole;
2-(4-methoxyphenyl)-4-acetyl-5-methylimidazole;
2-(3-methoxyphenyl)-4-acetyl-5-methylimidazole;
2-(2-methoxyphenyl)-4-acetyl-5-methylimidazole;
2-(2-methylphenyl)-4-acetyl-5-ethylimidazole;
2-(cyclopropyl)-4-acetyl-5-phenylimidazole;
2-(4-methylphenyl)-4-acetyl-5-t-butylimidazole; and
2-(4-methylphenyl)-4-acetylimidazole, there is obtained:

2-(phenyl)-4-(1-chloro-2-methylpropyl)-5-methylimidazole hydrochloride;
2-(3-methylphenyl)-4-(1-chloroethyl)-5-methylimidazole hydrochloride;
2-(2-methylphenyl)-4-(1-chloroethyl)-5-methylimidazole hydrochloride;
2-(4-t-butylphenyl)-4-(1-chloroethyl)-5-methylimidazole hydrochloride;
2-(3-t-butylphenyl)-4-(1-chloroethyl)-5-methylimidazole hydrochloride;
2-(2-t-butylphenyl)-4-(1-chloroethyl)-5-methylimidazole hydrochloride;
2-(4-chlorophenyl)-4-(1-chloroethyl)-5-methylimidazole hydrochloride;
2-(3-chlorophenyl)-4-(1-chloroethyl)-5-methylimidazole hydrochloride;
2-(2-chlorophenyl)-4-(1-chloroethyl)-5-methylimidazole hydrochloride;
2-(4-methoxyphenyl)-4-(1-chloroethyl)-5-methylimidazole hydrochloride;
2-(3-methoxyphenyl)-4-(1-chloroethyl)-5-methylimidazole hydrochloride;
2-(2-methoxyphenyl)-4-(1-chloroethyl)-5-methylimidazole hydrochloride;
2-(2-methylphenyl)-4-(1-chloroethyl)-5-ethylimidazole hydrochloride;
2-(cyclopropyl)-4-(1-chloroethyl)-5-phenylimidazole hydrochloride;
2-(4-methylphenyl)-4-(1-chloroethyl)-5-t-butylimidazole hydrochloride; and
2-(4-methylphenyl)-4-(1-chloroethyl)-imidazole hydrochloride.

2D. Formula A Where $R^1$ is Phenyl; $R^2$ is Methyl; $R^3$ is Methyl; $R^4$ and $R^5$ are Phenyl; m is 2; n is 0; and q is 0

14 Grams (0.052 mol) of N-(diphenylmethyl)piperazine and 6 grams (0.15 mol) of sodium hydroxide were dissolved in 180 ml of a mixture of ethanol:water 60:40. The mixture was heated to reflux, then 2-phenyl-4-(1-chloroethyl)-5-methylimidazole hydrochloride in 180 milliliters of ethanol:water 60:40 were added dropwise. After 4 to 5 hours under reflux, the reaction mixture was allowed to cool to room temperature. The oil that separated was washed twice with water, then dissolved in ether and hydrochloric acid was added. The precipitate was recrystallized from ethanol to give 1-diphenylmethyl-4-[1-(2-phenyl-5-methyl-1H-imidazol-4-yl)ethyl]piperazine trihydrochloride, which melted at 215° C.

2E. Formula A Where $R^3$ is Methyl; $R^4$ and $R^5$ are Phenyl; m is 2; n is 0; q is 0; and Varying $R^1$ and $R^2$ Similarly, following the procedure of Part D above, but replacing 2-phenyl-4-(1-chloroethyl)-5-methylimidazole hydrochloride with:

2-(phenyl)-4-(1-chloro-2-methylpropyl)-5-methylimidazole hydrochloride;
2-(phenyl)-4-(1-chloroethyl)-5-methylimidazole hydrochloride;
2-methyl-4-(1-chloroethyl)-5-methylimidazole hydrochloride;
2-t-butyl-4-(1-chloroethyl)-5-methylimidazole hydrochloride;
2-(3-methylphenyl)-4-(1-chloroethyl)-5-methylimidazole hydrochloride;
2-(2-methylphenyl)-4-(1-chloroethyl)-5-methylimidazole hydrochloride;
2-(4-t-butylphenyl)-4-(1-chloroethyl)-5-methylimidazole hydrochloride;
2-(3-t-butylphenyl)-4-(1-chloroethyl)-5-methylimidazole hydrochloride;
2-(2-t-butylphenyl)-4-(1-chloroethyl)-5-methylimidazole hydrochloride;
2-(4-chlorophenyl)-4-(1-chloroethyl)-5-methylimidazole hydrochloride;
2-(3-chlorophenyl)-4-(1-chloroethyl)-5-methylimidazole hydrochloride;
2-(2-chlorophenyl)-4-(1-chloroethyl)-5-methylimidazole hydrochloride;
2-(4-methoxyphenyl)-4-(1-chloroethyl)-5-methylimidazole hydrochloride;
2-(3-methoxyphenyl)-4-(1-chloroethyl)-5-methylimidazole hydrochloride;
2-(2-methoxyphenyl)-4-(1-chloroethyl)-5-methylimidazole hydrochloride;
2-(2-methylphenyl)-4-(1-chloroethyl)-5-ethylimidazole hydrochloride;
2-(cyclopropyl)-4-(1-chloroethyl)-5-phenylimidazole hydrochloride;
2-(4-methylphenyl)-4-(1-chloroethyl)-5-t-butylimidazole hydrochloride; and
2-(4-methylphenyl)-4-(1-chloroethyl)-imidazole hydrochloride, there is obtained:

1-diphenylmethyl-4-[1-(2-phenyl-5-methyl-1H-imidazol-4-yl)ethyl]piperazine trihydrochloride;
1-diphenylmethyl-4-[1-(2-methyl-5-methyl-1H-imidazol-4-yl)ethyl]piperazine trihydrochloride;
1-diphenylmethyl-4-[1-(2-t-butyl-5-methyl-1H-imidazol-4-yl)ethyl]piperazine trihydrochloride;
1-diphenylmethyl-4-[1-(2-(3-methylphenyl)-5-methyl-1H-imidazol-4-yl)ethyl]piperazine trihydrochloride;
1-diphenylmethyl-4-[1-(2-(2-methylphenyl)-5-methyl-1H-imidazol-4-yl)ethyl]piperazine trihydrochloride;
1-diphenylmethyl-4-[1-(2-(4-t-butylphenyl)-5-methyl-1H-imidazol-4-yl)ethyl]piperazine trihydrochloride;
1-diphenylmethyl-4-[1-(2-(3-t-butylphenyl)-5-methyl-1H-imidazol-4-yl)ethyl]piperazine trihydrochloride;
1-diphenylmethyl-4-[1-(2-(2-t-butylphenyl)-5-methyl-1H-imidazol-4-yl)ethyl]piperazine trihydrochloride;
1-diphenylmethyl-4-[1-(2-(4-chlorophenyl)-5-methyl-1H-imidazol-4-yl)ethyl]piperazine trihydrochloride;
1-diphenylmethyl-4-[1-(2-(3-chlorophenyl)-5-methyl-1H-imidazol-4-yl)ethyl]piperazine trihydrochloride;
1-diphenylmethyl-4-[1-(2-(2-chlorophenyl)-5-methyl-1H-imidazol-4-yl)ethyl]piperazine trihydrochloride;
1-diphenylmethyl-4-[1-(2-(4-methoxyphenyl)-5-methyl-1H-imidazol-4-yl)ethyl]piperazine trihydrochloride;
1-diphenylmethyl-4-[1-(2-(3-methoxyphenyl)-5-methyl-1H-imidazol-4-yl)ethyl]piperazine trihydrochloride;
1-diphenylmethyl-4-[1-(2-(2-methoxyphenyl)-5-methyl-1H-imidazol-4-yl)ethyl]piperazine trihydrochloride;
1-diphenylmethyl-4-[1-(2-(2-methylphenyl)-5-ethyl-1H-imidazol-4-yl)ethyl]piperazine trihydrochloride;
1-diphenylmethyl-4-[1-(2-(2-cyclopropyl)-5-phenyl-1H-imidazol-4-yl)ethyl]piperazine trihydrochloride;
1-diphenylmethyl-4-[1-(2-(4-methylphenyl)-5-t-butyl-1H-imidazol-4-yl)ethyl]piperazine trihydrochloride; and
1-diphenylmethyl-4-[1-(2-(4-methylphenyl)-1H-imidazol-4-yl)ethyl]piperazine trihydrochloride.

2F. Formula A Where $R^1$ is Phenyl; $R^2$ is Methyl; $R^3$ is Methyl; m is 2; n is 0; and Varying q, $R^4$ and $R^5$ Similarly, following the procedure of Part D above, but replacing N-(diphenylmethyl)piperazine with:
N-[di-(2-methylphenyl)methyl]piperazine;
N-[di-(3-methylphenyl)methyl]piperazine;
N-[di-(4-methylphenyl)methyl]piperazine;
N-[di-(2-t-butylphenyl)methyl]piperazine;
N-[di-(3-t-butylphenyl)methyl]piperazine;
N-[di-(4-t-butylphenyl)methyl]piperazine;
N-[di-(2-methoxyphenyl)methyl]piperazine;
N-[di-(3-methoxyphenyl)methyl]piperazine;
N-[di-(4-methoxyphenyl)methyl]piperazine;
N-[di-(2-chlorophenyl)methyl]piperazine;
N-[di-(3-chlorophenyl)methyl]piperazine;
N-[di-(4-chlorophenyl)methyl]piperazine;
N-[di-(4-fluorophenyl)methyl]piperazine;
N-benzylpiperazine;
N-[1-(4-chlorophenyl)-1-(phenyl)methyl]piperazine;
N-(2,2-diphenylethyl)piperazine;
N-[3-(phenyl)-3-(4-methoxyphenyl)propyl]piperazine; and
N-(4,4-diphenylbutyl)piperazine, there is obtained:

1-[di-(2-methylphenyl)methyl]-4-[1-(2-phenyl-5-methyl-1H-imidazol-4-yl)ethyl]piperazine trihydrochloride;
1-[di-(3-methylphenyl)methyl]-4-[1-(2-phenyl-5-methyl-1H-imidazol-4-yl)ethyl]piperazine trihydrochloride;
1-[di-(4-methylphenyl)methyl]-4-[1-(2-phenyl-5-methyl-1H-imidazol-4-yl)ethyl]piperazine trihydrochloride;
1-[di-(2-t-butylphenyl)methyl]-4-[1-(2-phenyl-5-methyl-1H-imidazol-4-yl)ethyl]piperazine trihydrochloride;
1-[di-(3-t-butylphenyl)methyl]-4-[1-(2-phenyl-5-methyl-1H-imidazol-4-yl)ethyl]piperazine trihydrochloride;
1-[di-(4-t-butylphenyl)methyl]-4-[1-(2-phenyl-5-methyl-1H-imidazol-4-yl)ethyl]piperazine trihydrochloride;
1-[di-(2-methoxyphenyl)methyl]-4-[1-(2-phenyl-5-methyl-1H-imidazol-4-yl)ethyl]piperazine trihydrochloride;
1-[di-(3-methoxyphenyl)methyl]-4-[1-(2-phenyl-5-methyl-1H-imidazol-4-yl)ethyl]piperazine trihydrochloride;

1-[di-(4-methoxyphenyl)methyl]-4-[1-(2-phenyl-5-methyl-1H-imidazol-4-yl)ethyl]piperazine trihydrochloride;

1-[di-(2-chlorophenyl)methyl]-4-[1-(2-phenyl-5-methyl-1H-imidazol-4-yl)ethyl]piperazine trihydrochloride;

1-[di-(3-chlorophenyl)methyl]-4-[1-(2-phenyl-5-methyl-1H-imidazol-4-yl)ethyl]piperazine trihydrochloride;

1-[di-(4-chlorophenyl)methyl]-4-[1-(2-phenyl-5-methyl-1H-imidazol-4-yl)ethyl]piperazine trihydrochloride;

1-[di-(4-fluorophenyl)methyl]-4-[1-(2-phenyl-5-methyl-1H-imidazol-4-yl)ethyl]piperazine trihydrochloride;

1-benzyl-4-[1-(2-phenyl-5-methyl-1H-imidazol-4-yl)ethyl]piperazine trihydrochloride;

1-[(4-chlorophenyl)-1-(phenyl)methyl]-4-[1-(2-phenyl-5-methyl-1H-imidazol-4-yl)ethyl]piperazine trihydrochloride;

1-(2,2-diphenylethyl)-4-[1-(2-phenyl-5-methyl-1H-imidazol-4-yl)ethyl]piperazine trihydrochloride;

1-[3-(phenyl)-3-(4-methoxyphenyl)propyl]-4-[1-(2-phenyl-5-methyl-1H-imidazol-4-yl)ethyl]piperazine trihydrochloride; and 1-(4,4-diphenylbutyl)-4-[1-(2-phenyl-5-methyl-1H-imidazol-4-yl)ethyl]piperazine trihydrochloride.

2G. Formula A Where $R^3$ is Methyl; m is 2; n is 0; and Varying $R^1$; $R^2$; $R^4$; $R^5$ and q Similarly, by following the procedures of Parts E and F above, other compounds of Formula A where $R^3$ is methyl, m is 2, and n is 0 are obtained, such as:

1-benzyl-4-[1-(2-methyl-5-ethyl-1H-imidazol-4-yl)ethyl]piperazine trihydrochloride;

1-[(4-chlorophenyl)-1-(phenyl)methyl]-4-[1-(2-phenyl-5-(4-methylphenyl)-1H-imidazol-4-yl)ethyl]piperazine trihydrochloride;

1-(2,2-diphenylethyl)-4-[1-(2-cyclohexyl-5-phenyl-1H-imidazol-4-yl)ethyl]piperazine trihydrochloride;

1-[3-(phenyl)-3-(4-methoxyphenyl)propyl]-4-[1-(2-(3-methoxyphenyl)-5-propyl-1H-imidazol-4-yl)ethyl]piperazine trihydrochloroide; and 1-(4,4-diphenylbutyl)-4-[1-(5-(2-methylphenyl)-1H-imidazol-4-yl)ethyl]piperazine trihydrochloride.

2H. Formula A Where $R^3$ is Lower Alkyl Other Than Methyl

Similarly, following the procedure of Part D above, but replacing 2-phenyl-4-(1-chloroethyl)-5-methylimidazole hydrochloride with:

2-phenyl-4-(1-chloropropyl)-5-methylimidazole hydrochloride; and 2-phenyl-4-(1-chlorobutyl)-5-methylimidazole hydrochloride, there is obtained:

1-diphenylmethyl-4-[1-(2-phenyl-5-methyl-1H-imidazol-4-yl)propyl]piperazine trihydrochloride; and 1-diphenylmethyl-4-[1-(2-phenyl-5-methyl-1H-imidazol-4-yl)butyl]piperazine trihydrochloride.

2I. Formula A Varying m

Similarly, by following the procedures of Parts A-H above, but replacing the piperazines there-used with the corresponding diazepines, the compounds of Formula A wherein m is 3 are obtained.

EXAMPLE 3

1-Diphenylmethyl-4-[2-(2-phenyl-5-methyl-1H-imidazol-4-yl)-2-hydroxyethyl]piperazine trihydrochloride and Derivatives Thereof 3A. Formula 9 Where $R^1$ is Phenyl; $R^2$ is Methyl; $R^4$ and $R^5$ are Phenyl; m is 2; and q is 0

10 Grams (0.036 mol) of 2-phenyl-4-(2-bromoethanoyl)-5-methyl-1H-imidazole and 8.5 grams (0.034 mol) of N-(diphenylmethyl)piperazine and 5 grams (0.036 mol) of potassium carbonate were added to 300 ml of ethanol. The mixture was refluxed under stirring overnight. After cooling, the salts were removed by filtration and the solvent was removed under reduced pressure. The residue was extracted by dichloromethane and washed twice with water. The organic layer was dried over sodium sulfate and evaporated. Trituration of the residue with ethanol gave a white precipitate, 1-diphenylmethyl-4-[2-(2-phenyl-5-methyl-1H-imidazol-4-yl)-2-oxoethyl]piperazine, which was used in the next reaction step without further purification.

3B. TriHCl Salt of Formula A Where $R^1$ is Phenyl; $R^2$ is Methyl; $R^3$ is Hydroxy; $R^4$ and $R^5$ are Phenyl; m is 2; n is 1; and q is 0

6 Grams of 1-diphenylmethyl-4-[2-(2-phenyl-5-methyl-1H-imidazol-4-yl)-2-oxoethyl]piperazine was dissolved in 100 ml of methanol. The reaction was cooled to 5° C. and then 2 grams (0.05 mol) of sodium borohydride was added portionwise. After stirring for 2 hours at room temperature, the mixture was evaporated off. The residue was extracted with dichloromethane and washed with water. Then the organic layer was dried over sodium sulphate and the solvent removed under reduced pressure. The crude material was then dissolved in diethyloxide and hydrochloric acid was added. The white precipitate was then removed by filtration and dried to give 1-diphenylmethyl-4-[2-(2-phenyl-5-methyl-1H-imidazol-4-yl)-2-hydroxyethyl]-piperazine trihydrochloride, which melted at 200° C.

3C. TriHCl Salt of Formula A Where $R^3$ is Hydroxy; $R^4$ and $R^5$ are Phenyl; m is 2; n is 1; q is 0; and Varying $R^1$ and $R^2$ Similarly, following the procedures of Parts A and B above, but replacing 2-phenyl-4-(2-bromo-ethanoyl)-5-methyl-1H-imidazole with:

2-(3-methylphenyl)-4-(2-bromoethanoyl)-5-methyl-1H-imidazole;

2-(2-methylphenyl)-4-(2-bromoethanoyl)-5-methyl-1H-imidazole;

2-(4-t-butylphenyl)-4-(2-bromoethanoyl)-5-methyl-1H-imidazole;

2-(3-t-butylphenyl)-4-(2-bromoethanoyl)-5-methyl-1H-imidazole;

2-(2-t-butylphenyl)-4-(2-bromoethanoyl)-5-methyl-1H-imidazole;

2-(4-chlorophenyl)-4-(2-bromoethanoyl)-5-methyl-1H-imidazole;

2-(3-chlorophenyl)-4-(2-bromoethanoyl)-5-methyl-1H-imidazole;

2-(2-chlorophenyl)-4-(2-bromoethanoyl)-5-methyl-1H-imidazole;

2-(4-methoxyphenyl)-4-(2-bromoethanoyl)-5-methyl-1H-imidazole;

2-(3-methoxyphenyl)-4-(2-bromoethanoyl)-5-methyl-1H-imidazole;

2-(2-methoxyphenyl)-4-(2-bromoethanoyl)-5-methyl-1H-imidazole;
2-(2-methylphenyl)-4-(2-bromoethanoyl)-5-ethyl-1H-imidazole;
2-(cyclohexyl)-4-(2-bromoethanoyl)-5-ethyl-1H-imidazole;
2-(4-methylphenyl)-4-(2-bromoethanoyl)-5-t-butyl-1H-imidazole; and
2-(4-methylphenyl)-4-(2-bromoethanoyl)-1H-imidazole, there is obtained:

1-diphenylmethyl-4-[2-(2-(3-methylphenyl)-5-methyl-1H-imidazol-4-yl)-2-hydroxyethyl]piperazine trihydrochloride;
1-diphenylmethyl-4-[2-(2-(2-methylphenyl)-5-methyl-1H-imidazol-4-yl)-2-hydroxyethyl]piperazine trihydrochloride;
1-diphenylmethyl-4-[2-(2-(4-t-butylphenyl)-5-methyl-1H-imidazol-4-yl)-2-hydroxyethyl]piperazine trihydrochloride;
1-diphenylmethyl-4-[2-(2-(3-t-butylphenyl)-5-methyl-1H-imidazol-4-yl)-2-hydroxyethyl]piperazine trihydrochloride;
1-diphenylmethyl-4-[2-(2-(2-t-butylphenyl)-5-methyl-1H-imidazol-4-yl)-2-hydroxyethyl]piperazine trihydrochloride;
1-diphenylmethyl-4-[2-(2-(4-chlorophenyl)-5-methyl-1H-imidazol-4-yl)-2-hydroxyethyl]piperazine trihydrochloride;
1-diphenylmethyl-4-[2-(2-(3-chlorophenyl)-5-methyl-1H-imidazol-4-yl)-2-hydroxyethyl]piperazine trihydrochloride;
1-diphenylmethyl-4-[2-(2-(2-chlorophenyl)-5-methyl-1H-imidazol-4-yl)-2-hydroxyethyl]piperazine trihydrochloride;
1-diphenylmethyl-4-[2-(2-(4-methoxyphenyl)-5-methyl-1H-imidazol-4-yl)-2-hydroxyethyl]piperazine trihydrochloride;
1-diphenylmethyl-4-[2-(2-(3-methoxyphenyl)-5-methyl-1H-imidazol-4-yl)-2-hydroxyethyl]piperazine trihydrochloride;
1-diphenylmethyl-4-[2-(2-(2-methoxyphenyl)-5-methyl-1H-imidazol-4-yl)-2-hydroxyethyl]piperazine trihydrochloride;
1-diphenylmethyl-4-[2-(2-(2-methylphenyl)-5-ethyl-1H-imidazol-4-yl)-2-hydroxyethyl]piperazine trihydrochloride;
1-diphenylmethyl-4-[2-(2-cyclohexyl-5-ethyl-1H-imidazol-4-yl)-2-hydroxyethyl]piperazine trihydrochloride;
1-diphenylmethyl-4-[2-(2-(4-methylphenyl)-5-t-butyl-1H-imidazol-4-yl)-2-hydroxyethyl]piperazine trihydrochloride; and
1-diphenylmethyl-4-[2-(2-(4-methylphenyl)-1H-imidazol-4-yl)-2-hydroxyethyl]piperazine trihydrochloride.

3D. TriHCl Salt of Formula A Where $R^1$ is Phenyl; $R^2$ is Methyl; $R^3$ is Hydroxy; m is 2; n is 1; q is 0; and Varying $R^4$ and $R^5$ Similarly, following the procedures of Parts A and B above, but replacing N-(diphenylmethyl)piperazine with:

N-[di-(2-methylphenyl)methyl]piperazine;
N-[di-(3-methylphenyl)methyl]piperazine;
N-[di-(4-methylphenyl)methyl]piperazine;
N-[di-(2-t-butylphenyl)methyl]piperazine;
N-[di-(3-t-butylphenyl)methyl]piperazine;
N-[di-(4-t-butylphenyl)methyl]piperazine;
N-[di-(2-methoxyphenyl)methyl]piperazine;
N-[di-(3-methoxyphenyl)methyl]piperazine;
N-[di-(4-methoxyphenyl)methyl]piperazine;
N-[di-(2-chlorophenyl)methyl]piperazine;
N-[di-(3-chlorophenyl)methyl]piperazine;
N-[di-(4-chlorophenyl)methyl]piperazine;
N-[di-(4-fluorophenyl)methyl]piperazine;
N-benzylpiperazine;
N-[1-(4-chlorophenyl)-1-(phenyl)methyl]piperazine;
N-(2,2-diphenylethyl)piperazine;
N-[3-(phenyl)-3-(4-methoxyphenyl)propyl]piperazine; and
N-(4,4-diphenylbutyl)piperazine,
there is obtained:

1-[di-(2-methylphenyl)methyl]-4-[2-(2-phenyl-5-methyl-1H-imidazol-4-yl)-2-hydroxyethyl]piperazine trihydrochloride;
1-[di-(3-methylphenyl)methyl]-4-[2-(2-phenyl-5-methyl-1H-imidazol-4-yl)-2-hydroxyethyl]piperazine trihydrochloride;
1-[di-(4-methylphenyl)methyl]-4-[2-(2-phenyl-5-methyl-1H-imidazol-4-yl)-2-hydroxyethyl]piperazine trihydrochloride;
1-[di-(2-t-butylphenyl)methyl]-4-[2-(2-phenyl-5-methyl-1H-imidazol-4-yl)-2-hydroxyethyl]piperazine trihydrochloride;
1-[di-(3-t-butylphenyl)methyl]-4-[2-(2-phenyl-5-methyl-1H-imidazol-4-yl)-2-hydroxyethyl]piperazine trihydrochloride;
1-[di-(4-t-butylphenyl)methyl]-4-[2-(2-phenyl-5-methyl-1H-imidazol-4-yl)-2-hydroxyethyl]piperazine trihydrochloride;
1-[di-(2-methoxyphenyl)methyl]-4-[2-(2-phenyl-5-methyl-1H-imidazol-4-yl)-2-hydroxyethyl]piperazine trihydrochloride;
1-[di-(3-methoxyphenyl)methyl]-4-[2-(2-phenyl-5-methyl-1H-imidazol-4-yl)-2-hydroxyethyl]piperazine trihydrochloride;
1-[di-(4-methoxyphenyl)methyl]-4-[2-(2-phenyl-5-methyl-1H-imidazol-4-yl)-2-hydroxyethyl]piperazine trihydrochloride;
1-[di-(2-chlorophenyl)methyl]-4-[2-(2-phenyl-5-methyl-1H-imidazol-4-yl)-2-hydroxyethyl]piperazine trihydrochloride;
1-[di-(3-chlorophenyl)methyl]-4-[2-(2-phenyl-5-methyl-1H-imidazol-4-yl)-2-hydroxyethyl]piperazine trihydrochloride;
1-[di-(4-chlorophenyl)methyl]-4-[2-(2-phenyl-5-methyl-1H-imidazol-4-yl)-2-hydroxyethyl]piperazine trihydrochloride;
1-[di-(4-fluorophenyl)methyl]-4-[2-(2-phenyl-5-methyl-1H-imidazol-4-yl)-2-hydroxyethyl]piperazine trihydrochloride;
1-benzyl-4-[2-(2-phenyl-5-methyl-1H-imidazol-4-yl)ethyl]piperazine trihydrochloride;
1-[(4-chlorophenyl)-1-(phenyl)methyl]-4-[2-(2-phenyl-5-methyl-1H-imidazol-4-yl)-2-hydroxyethyl]piperazine trihydrochloride;
1-(2,2-diphenylethyl)-4-[2-(2-phenyl-5-methyl-1H-imidazol-4-yl)-2-hydroxyethyl]piperazine trihydrochloride;
1-[3-(phenyl)-3-(4-methoxyphenyl)propyl]-4-[2-(2-phenyl-5-methyl-1H-imidazol-4-yl)-2-hydroxyethyl]piperazine trihydrochloride; and 1-(4,4-diphenylbutyl)-4-[2-(2-phenyl-5-methyl-1H-imidazol-4-yl)-2-hydroxyethyl]piperazine trihydrochloride.

3E. TriHCl Salt of Formula A Where $R^3$ is Hydroxy; m is 2; n is 1 or 2; and Varying $R^1$, $R^2$; $R^4$; $R^5$ and q Similarly, by following the procedures of Parts C and D above, other compounds of Formula A where $R^3$ is hydroxy, m is 2, and n is 1 or 2 are obtained, such as:

1-[(4-chlorophenyl)-1-(phenyl)methyl]-4-[2-(2-methyl-5-phenyl-1H-imidazol-4-yl)-2-hydroxyethyl]piperazine trihydrochloride;

1-[(4-chlorophenyl)-1-(phenyl)methyl]-4-[3-(2-phenyl-5-methyl-1H-imidazol-4-yl)-3-hydroxypropyl]piperazine trihydrochloride, by starting with 2-phenyl-4-(3-bromopropanoyl)-5-methyl-1H-imidazole in part 3A;

1-(2,2-diphenylethyl)-4-[2-(2-(4-methylphenyl)-5-methyl-1H-imidazol-4-yl)-2-hydroxyethyl]piperazine trihydrochloride;

1-[3-(phenyl)-3-(4-methoxyphenyl)propyl]-4-[2-(2-cyclopropyl-5-ethyl-1H-imidazol-4-yl)-2-hydroxyethyl]piperazine trihydrochloride; and 1-(4,4-diphenylbutyl)-4-[2-(5-methyl-1H-imidazol-4-yl)-2-hydroxyethyl]piperazine trihydrochloride.

3F. Formula A Varying m

Similarly, by following the procedures of Parts A-E above, but replacing the piperazines there-used with the corresponding diazepines, the compounds of Formula A wherein m is 3 are obtained.

EXAMPLE 4

1-Diphenylmethyl-4-[1-(2-phenyl-5-methyl-1H-imidazol-4-yl)-2-methylpropyl]piperazine and Derivatives Thereof 4A. Formula 12 Where $R^1$ is Phenyl; $R^2$ is Methyl; and $R^6$ is Isopropyl 35 Grams (0.45 mol) of 2-chloropropane was added to 10.8 g (0.45 mol) of magnesium in 100 ml of diethyloxyde. Then 55.8 g (0.3 mol) of 2-phenyl-4-formyl-5-methyl-1H-imidazole in 100 ml of THF were added. At the end of the addition, the mixture was refluxed for 30 minutes and then cooled and poured on ice water. The aqueous layer was extracted twice with 100 ml of diethyl ether. Evaporation of the solvent gave a residue which was recrystallized in ethanol to yield 40 grams of 2-phenyl-4-(1-hydroxy-2-methylpropyl)-5-methyl-1H-imidazole, which melted at 214° C.

4B. Formula 12 Where $R^6$ is Isopropyl; and Varying $R^1$ and $R^2$

Similarly, following the procedure of Part A above, but replacing 2-phenyl-4-formyl-5-methyl-1H-imidazole with:

2-(3-methylphenyl)-5-methyl-4-formyl-1H-imidazole;
2-(2-methylphenyl)-5-methyl-4-formyl-1H-imidazole;
2-(4-t-butylphenyl)-5-methyl-4-formyl-1H-imidazole;
2-(3-t-butylphenyl)-5-methyl-4-formyl-1H-imidazole;
2-(2-t-butylphenyl)-5-methyl-4-formyl-1H-imidazole;
2-(4-chlorophenyl)-5-methyl-4-formyl-1H-imidazole;
2-(3-chlorophenyl)-5-methyl-4-formyl-1H-imidazole;
2-(2-chlorophenyl)-5-methyl-4-formyl-1H-imidazole;
2-(4-methoxyphenyl)-5-methyl-4-formyl-1H-imidazole;
2-(3-methoxyphenyl)-5-methyl-4-formyl-1H-imidazole;
2-(2-methoxyphenyl)-5-methyl-4-formyl-1H-imidazole;
2-(2-methylphenyl)-5-ethyl-4-formyl-1H-imidazole;
2-(4-methylphenyl)-5-t-butyl-4-formyl-1H-imidazole;
2-(4-methylphenyl)-4-formyl-1H-imidazole,
2-(3,4-dimethoxyphenyl)-4-formyl-5-methyl-1H-imidazole;
2,5-di-(4-methylphenyl)-4-formyl-1H-imidazole;
2-(cyclopropyl)-4-formyl-5-methyl-1H-imidazole;
2-ethyl-4-formyl-5-methyl-1H-imidazole;
4-formyl-5-phenyl-1H-imidazole; and
2-methyl-4-formyl-5-(3-methoxyphenyl)-1H-imidazole, there is obtained:

2-(3-methylphenyl)-5-methyl-4-(1-hydroxy-2-methylpropyl)-1H-imidazole;
2-(2-methylphenyl)-5-methyl-4-(1-hydroxy-2-methylpropyl)-1H-imidazole;
2-(4-t-butylphenyl)-5-methyl-4-(1-hydroxy-2-methylpropyl)-1H-imidazole;
2-(3-t-butylphenyl)-5-methyl-4-(1-hydroxy-2-methylpropyl)-1H-imidazole;
2-(2-t-butylphenyl)-5-methyl-4-(1-hydroxy-2-methylpropyl)-1H-imidazole;
2-(4-chlorophenyl)-5-methyl-4-(1-hydroxy-2methylpropyl)-1H-imidazole;
2-(3-chlorophenyl)-5-methyl-4-(1-hydroxy-2-methylpropyl)-1H-imidazole;
2-(2-chlorophenyl)-5-methyl-4-(1-hydroxy-2-methylpropyl)-1H-imidazole;
2-(4-methoxyphenyl)-5-methyl-4-(1-hydroxy-2-methylpropyl)-1H-imidazole;
2-(3-methoxyphenyl)-5-methyl-4-(1-hydroxy-2-methylpropyl)-1H-imidazole;
2-(2-methoxyphenyl)-5-methyl-4-(1-hydroxy-2-methylpropyl)-1H-imidazole;
2-(2-methylphenyl)-5-ethyl-4-(1-hydroxy-2-methylpropyl)-1H-imidazole;
2-(4-methylphenyl)-5-t-butyl-4-(1-hydroxy-2-methylpropyl)-1H-imidazole;
2-(4-methylphenyl)-4-(1-hydroxy-2-methylpropyl)-1H-imidazole;
2-(3,4-dimethoxyphenyl)-5-methyl-4-(1-hydroxy-2-methylpropyl)-1H-imidazole;
2,5-di-(4-methylphenyl)-4-(1-hydroxy-2-methylpropyl)-1H-imidazole;
2-cyclopropyl-5-methyl-4-(1-hydroxy-2-methylpropyl)-1H-imidazole;
2-ethyl-5-methyl-4-(1-hydroxy-2-methylpropyl)-1H-imidazole;
4-(1-hydroxy-2-methylpropyl)-5-phenyl-1H-imidazole; and
2-methyl-5-(3-methoxyphenyl)-4-(1-hydroxy-2-methylpropyl)-1H-imidazole.

4C. Formula 13 Where $R^1$ is Phenyl; $R^2$ is Methyl; $R^6$ is Isopropyl; and X is Chloro 27 g of 2-phenyl-4-(1-hydroxy-2-methylpropyl)-5-methyl-1H-imidazole are dissolved in 700 ml of chloroform with 44 ml of $SOCl_2$ and refluxed for 5 hours. 2-Phenyl-5-methyl-4-(1-chloro-2-methylpropyl)-1H-imidazole hydrochloride is isolated in quantitative yield.

4D. Formula 13 Where $R^6$ is Isopropyl; X is Chloro; and Varying $R^1$ and $R^2$ Similarly, following the procedure of Part C above, but replacing 2-phenyl-5-methyl-4-(1-hydroxy-2-methylpropyl)-1H-imidazole with:

2-(3-methylphenyl)-5-methyl-4-(1-hydroxy-2-methylpropyl)-1H-imidazole;
2-(2-methylphenyl)-5-methyl-4-(1-hydroxy-2-methylpropyl)-1H-imidazole;

2-(4-t-butylphenyl)-5-methyl-4-(1-hydroxy-2-methyl-propyl)-1H-imidazole;
2-(3-t-butylphenyl)-5-methyl-4-(1-hydroxy-2-methyl-propyl)-1H-imidazole;
2-(2-t-butylphenyl)-5-methyl-4-(1-hydroxy-2-methyl-propyl)-1H-imidazole;
2-(4-chlorophenyl)-5-methyl-4-(1-hydroxy-2-methyl-propyl)-1H-imidazole;
2-(3-chlorophenyl)-5-methyl-4-(1-hydroxy-2-methyl-propyl)-1H-imidazole;
2-(2-chlorophenyl)-5-methyl-4-(1-hydroxy-2-methyl-propyl)-1H-imidazole;
2-(4-methoxyphenyl)-5-methyl-4-(1-hydroxy-2-methyl-propyl)-1H-imidazole;
2-(3-methoxyphenyl)-5-methyl-4-(1-hydroxy-2-methyl-propyl)-1H-imidazole;
2-(2-methoxyphenyl)-5-methyl-4-(1-hydroxy-2-methyl-propyl)-1H-imidazole;
2-(2-methylphenyl)-5-ethyl-4-(1-hydroxy-2-methyl-propyl)-1H-imidazole;
2-(4-methylphenyl)-5-t-butyl-4-(1-hydroxy-2-methyl-propyl)-1H-imidazole hydrochloride;
2-(4-methylphenyl)-4-(1-hydroxy-2-methylpropyl)-1H-imidazole hydrochloride;
2-(3,4-dimethoxyphenyl)-4-(1-hydroxy-2-methyl-propyl)-5-methyl-1H-imidazole;
2,5-di-(4-methylphenyl)-4-(1-hydroxy-2-methylpropyl)-1H-imidazole;
2-cyclopropyl-5-methyl-4-(1-hydroxy-2-methylpropyl)-1H-imidazole;
2-ethyl-5-methyl-4-(1-hydroxy-2-methylpropyl)-1H-imidazole;
4-(1-hydroxy-2-methylpropyl)-5-phenyl-1H-imidazole; and
2-methyl-4-(1-hydroxy-2-methylpropyl)-5-(3-methoxyphenyl)-1H-imidazole, there is obtained:

2-(3-methylphenyl)-5-methyl-4-(1-chloro-2-methyl-propyl)-1H-imidazole hydrochloride;
2-(2-methylphenyl)-5-methyl-4-(1-chloro-2-methyl-propyl)-1H-imidazole hydrochloride;
2-(4-t-butylphenyl)-5-methyl-4-(1-chloro-2-methyl-propyl)-1H-imidazole hydrochloride;
2-(3-t-butylphenyl)-5-methyl-4-(1-chloro-2-methyl-propyl)-1H-imidazole hydrochloride;
2-(2-t-butylphenyl)-5-methyl-4-(1-chloro-2-methyl-propyl)-1H-imidazole hydrochloride;
2-(4-chlorophenyl)-5-methyl-4-(1-chloro-2-methyl-propyl)-1H-imidazole hydrochloride;
2-(3-chlorophenyl)-5-methyl-4-(1-chloro-2-methyl-propyl)-1H-imidazole hydrochloride;
2-(2-chlorophenyl)-5-methyl-4-(1-chloro-2-methyl-propyl)-1H-imidazole hydrochloride;
2-(4-methoxyphenyl)-5-methyl-4-(1-chloro-2-methyl-propyl)-1H-imidazole hydrochloride;
2-(3-methoxyphenyl)-5-methyl-4-(1-chloro-2-methyl-propyl)-1H-imidazole hydrochloride;
2-(2-methoxyphenyl)-5-methyl-4-(1-chloro-2-methyl-propyl)-1H-imidazole hydrochloride;
2-(2-methylphenyl)-5-ethyl-4-(1-chloro-2-methyl-propyl)-1H-imidazole hydrochloride;
2-(4-methylphenyl)-5-t-butyl-4-(1-chloro-2-methyl-propyl)-1H-imidazole hydrochloride;
2-(4-methylphenyl)-4-(1-chloro-2-methylpropyl)-1H-imidazole hydrochloride;
2-(3,4-dimethoxyphenyl)-5-methyl-4-(1-chloro-2-methylpropyl)-1H-imidazole hydrochloride;
2,5-di-(4-methylphenyl)-4-(1-chloro-2-methylpropyl)-1H-imidazole hydrochloride;
2-cyclopropyl-5-methyl-4-(1-chloro-2-methylpropyl)-1H-imidazole hydrochloride;
2-ethyl-5-methyl-4-(1-chloro-2-methylpropyl)-1H-imidazole;
4-(1-chloro-2-methylpropyl)-5-phenyl-1H-imidazole hydrochloride; and
2-methyl-5-(3-methoxyphenyl)-4-(1-chloro-2-methyl-propyl)-1H-imidazole hydrochloride.

4E. TriHCl Salt of Formula A Where $R^1$ is Phenyl; $R^2$ is Methyl; $R^3$ is Isopropyl; $R^4$ and $R^5$ are Phenyl; m is 2; n is 0; and q is 0

14 Grams (0.05 mol) of diphenylmethyl-4-piperazine and 6 grams (0.15 mol) of sodium hydroxide are dissolved in 180 ml of a mixture of ethanol:water 60:40. The mixture is heated to reflux, then 2-phenyl-5-methyl-4-(1-chloro-2-methylpropyl)-1H-imidazole hydrochloride in 180 milliliters of ethanol:water 60:40 are added dropwise. After 4 to 5 hours under reflux, the reaction mixture is allowed to cool to room temperature. The oil that separated is washed twice with water, then dissolved in ether and hydrochloric acid is added. The precipitate is recrystallized from ethanol to give 1-diphenylmethyl-4-[1-(2-phenyl-5-methyl-1H-imidazole-4-yl)-2-methylpropyl]piperazine trihydrochloride.

4F. TriHCl Salt of Formula A Where $R^3$ is Isopropyl; $R^4$ and $R^5$ are Phenyl; m is 2; n is 0; q is 0; and Varying $R^1$ and $R^2$ Similarly, following the procedure of Part E above, but replacing 2-phenyl-5-methyl-4-(1-chloro-2-methyl-propyl)-1H-imidazole hydrochloride with:

2-(3-methylphenyl)-5-methyl-4-(1-chloro-2-methyl-propyl)-1H-imidazole hydrochloride;
2-(2-methylphenyl)-5-methyl-4-(1-chloro-2-methyl-propyl)-1H-imidazole hydrochloride;
2-(4-t-butylphenyl)-5-methyl-4-(1-chloro-2-methyl-propyl)-1H-imidazole hydrochloride;
2-(3-t-butylphenyl)-5-methyl-4-(1-chloro-2-methyl-propyl)-1H-imidazole hydrochloride;
2-(2-t-butylphenyl)-5-methyl-4-(1-chloro-2-methyl-propyl)-1H-imidazole hydrochloride;
2-(4-chlorophenyl)-5-methyl-4-(1-chloro-2-methyl-propyl)-1H-imidazole hydrochloride;
2-(3-chlorophenyl)-5-methyl-4-(1-chloro-2-methyl-propyl)-1H-imidazole hydrochloride;
2-(2-chlorophenyl)-5-methyl-4-(1-chloro-2-methyl-propyl)-1H-imidazole hydrochloride;
2-(4-methoxyphenyl)-5-methyl-4-(1-chloro-2-methyl-propyl)-1H-imidazole hydrochloride;
2-(3-methoxyphenyl)-5-methyl-4-(1-chloro-2-methyl-propyl)-1H-imidazole hydrochloride;
2-(2-methoxyphenyl)-5-methyl-4-(1-chloro-2-methyl-propyl)-1H-imidazole hydrochloride;
2-(2-methylphenyl)-5-ethyl-4-(1-chloro-2-methyl-propyl)-1H-imidazole hydrochloride;
2-(4-methylphenyl)-5-t-butyl-4-(1-chloro-2-methyl-propyl)-1H-imidazole hydrochloride;
2-(4-methylphenyl)-4-(1-chloro-2-methylpropyl)-1H-imidazole hydrochloride;
2-(3,4-dimethoxyphenyl)-4-(1-chloro-2-methylpropyl)-5-methyl-1H-imidazole hydrochloride;
2,5-di-(4-methylphenyl)-4-(1-chloro-2-methylpropyl)-1H-imidazole hydrochloride;

2-cyclopropyl-5-methyl-4-(1-chloro-2-methylpropyl)-1H-imidazole hydrochloride;
2-ethyl-5-methyl-4-(1-chloro-2-methylpropyl)-1H-imidazole;
4-(1-chloro-2-methylpropyl)-5-phenyl-1H-imidazole hydrochloride; and
2-methyl-4-(1-chloro-2-methylpropyl)-5-(3-methoxyphenyl)-1H-imidazole hydrochloride, there is obtained:

1-diphenylmethyl-4-[1-(2-(3-methylphenyl)-5-methyl-1H-imidazol-4-yl)-2-methylpropyl]piperazine trihydrochloride;
1-diphenylmethyl-4-[1-(2-(2-methylphenyl)-5-methyl-1H-imidazol-4-yl)-2-methylpropyl]piperazine trihydrochloride;
1-diphenylmethyl-4-[1-(2-(4-t-butylphenyl)-5-methyl-1H-imidazol-4-yl)-2-methylpropyl]piperazine trihydrochloride;
1-diphenylmethyl-4-[1-(2-(3-t-butylphenyl)-5-methyl-1H-imidazol-4-yl)-2-methylpropyl]piperazine trihydrochloride;
1-diphenylmethyl-4-[1-(2-(2-t-butylphenyl)-5-methyl-1H-imidazol-4-yl)-2-methylpropyl]piperazine trihydrochloride;
1-diphenylmethyl-4-[1-(2-(4-chlorophenyl)-5-methyl-1H-imidazol-4-yl)-2-methylpropyl]piperazine trihydrochloride;
1-diphenylmethyl-4-[1-(2-(3-chlorophenyl)-5-methyl-1H-imidazol-4-yl)-2-methylpropyl]piperazine trihydrochloride;
1-diphenylmethyl-4-[1-(2-(2-chlorophenyl)-5-methyl-1H-imidazol-4-yl)-2-methylpropyl]piperazine trihydrochloride;
1-diphenylmethyl-4-[1-(2-(4-methoxyphenyl)-5-methyl-1H-imidazol-4-yl)-2-methylpropyl]piperazine trihydrochloride;
1-diphenylmethyl-4-[1-(2-(3-methoxyphenyl)-5-methyl-1H-imidazol-4-yl)-2-methylpropyl]piperazine trihydrochloride;
1-diphenylmethyl-4-[1-(2-(2-methoxyphenyl)-5-methyl-1H-imidazol-4-yl)-2-methylpropyl]piperazine trihydrochloride;
1-diphenylmethyl-4-[1-(2-(2-methylphenyl)-5-ethyl-1H-imidazol-4-yl)-2-methylpropyl]piperazine trihydrochloride;
1-diphenylmethyl-4-[1-(2-(4-methylphenyl)-5-t-butyl-1H-imidazol-4-yl)-2-methylpropyl]piperazine trihydrochloride;
1-diphenylmethyl-4-[1-(2-(4-methylphenyl)-1H-imidazol-4-yl)-2-methylpropyl]piperazine trihydrochloride;
1-diphenylmethyl-4-[1-(2-(3,4-dimethoxyphenyl)-5-methyl-1H-imidazol-4-yl)-2-methylpropyl]piperazine trihydrochloride;
1-diphenylmethyl-4-[1(2,5-di-(4-methylphenyl)-1H-imidazol-4-yl)-2-methylpropyl]piperazine trihydrochloride;
1-diphenylmethyl-4-[1-(2-cyclopropyl-5-methyl-1H-imidazol-4-yl)-2-methylpropyl]piperazine trihydrochloride;
1-diphenylmethyl-4-[1-(2-ethyl-5-methyl-1H-imidazol-4-yl)-2-methylpropyl]piperazine trihydrochloride;
1-diphenylmethyl-4-[1-(5-phenyl-1H-imidazol-4-yl)-2-methylpropyl]piperazine trihydrochloride; and
1-diphenylmethyl-4-[1-(2-methyl-5-(3-methoxyphenyl)-1H-imidazol-4-yl)-2-methylpropyl]piperazine trihydrochloride.

4G. Formula A Where $R^3$ is Isopropyl, Varying q, $R^4$ and $R^5$

Similarly, following the procedure of Part E above, but replacing N-(diphenylmethyl)piperazine with:

N-[di-(2-methylphenyl)methyl]piperazine;
N-[di-(3-methylphenyl)methyl]piperazine;
N-[di-(4-methylphenyl)methyl]piperazine;
N-[di-(2-t-butylphenyl)methyl]piperazine;
N-[di-(3-t-butylphenyl)methyl]piperazine;
N-[di-(4-t-butylphenyl)methyl]piperazine;
N-[di-(2-methoxyphenyl)methyl]piperazine;
N-[di-(3-methoxyphenyl)methyl]piperazine;
N-[di-(4-methoxyphenyl)methyl]piperazine;
N-[di-(2-chlorophenyl)methyl]piperazine;
N-[di-(3-chlorophenyl)methyl]piperazine;
N-[di-(4-chlorophenyl)methyl]piperazine;
N-[di-(4-fluorophenyl)methyl]piperazine;
N-benzylpiperazine;
N-[1-(4-chlorophenyl)-1-(phenyl)methyl]piperazine;
N-(2,2-diphenylethyl)piperazine;
N-[3-(phenyl)-3-(4-methoxyphenyl)propyl]piperazine; and
N-(4,4-diphenylbutyl)piperazine, there is obtained:

1-[di-(2-methylphenyl)methyl]-4-[1-(2-phenyl-5-methyl-1H-imidazol-4-yl)-2-methylpropyl]piperazine trihydrochloride;
1-[di-(3-methylphenyl)methyl]-4-[1-(2-phenyl-5-methyl-1H-imidazol-4-yl)-2-methylpropyl]piperazine trihydrochloride;
1-[di-(4-methylphenyl)methyl]-4-[1-(2-phenyl-5-methyl-1H-imidazol-4-yl)-2-methylpropyl]piperazine trihydrochloride;
1-[di-(2-t-butylphenyl)methyl]-4-[1-(2-phenyl-5-methyl-1H-imidazol-4-yl)-2-methylpropyl]piperazine trihydrochloride;
1-[di-(3-t-butylphenyl)methyl]-4-[1-(2-phenyl-5-methyl-1H-imidazol-4-yl)-2-methylpropyl]piperazine trihydrochloride;
1-[di-(4-t-butylphenyl)methyl]-4-[1-(2-phenyl-5-methyl-1H-imidazol-4-yl)-2-methylpropyl]piperazine trihydrochloride;
1-[di-(2-methoxyphenyl)methyl]-4-[1-(2-phenyl-5-methyl-1H-imidazol-4-yl)-2-methylpropyl]piperazine trihydrochloride;
1-[di-(3-methoxyphenyl)methyl]-4-[1-(2-phenyl-5-methyl-1H-imidazol-4-yl)-2-methylpropyl]piperazine trihydrochloride;
1-[di-(4-methoxyphenyl)methyl]-4-[1-(2-phenyl-5-methyl-1H-imidazol-4-yl)-2-methylpropyl]piperazine trihydrochloride;
1-[di-(2-chlorophenyl)methyl]-4-[1-(2-phenyl-5-methyl-1H-imidazol-4-yl)-2-methylpropyl]piperazine trihydrochloride;
1-[di-(3-chlorophenyl)methyl]-4-[1-(2-phenyl-5-methyl-1H-imidazol-4-yl)-2-methylpropyl]piperazine trihydrochloride;
1-[di-(4-chlorophenyl)methyl]-4-[1-(2-phenyl-5-methyl-1H-imidazol-4-yl)-2-methylpropyl]piperazine trihydrochloride;

1-[di-(4-fluorophenyl)methyl]-4-[1-(2-phenyl-5-methyl-1H-imidazol-4-yl)-2-methylpropyl]piperazine trihydrochloride;

1-benzyl-4-[1-(2-phenyl-5-methyl-1H-imidazol-4-yl)-2-methylpropyl]piperazine trihydrochloride;

1-[1-(4-chlorophenyl)-1-(phenyl)methyl]-4-[1-(2-phenyl-5-methyl-1H-imidazol-4-yl)-2-methylpropyl]piperazine trihydrochloride;

1-(2,2-diphenylethyl)-4-[1-(2-phenyl-5-methyl-1H-imidazol-4-yl)-2-methylpropyl]piperazine trihydrochloride;

1-[3-(phenyl)-3-(4-methyoxyphenyl)propyl]-4-[1-(2-phenyl-5-methyl-1H-imidazol-4-yl)-2-methylpropyl]piperazine trihydrochloride; and 1-(4,4-diphenylbutyl)-4-[1-(2-phenyl-5-methyl-1H-imidazol-4-yl)-2-methylpropyl]piperazine trihydrochloride.

4H. TriHCl Salt of Formula A Where $R^3$ is Lower Alkyl Other Than Isopropyl

Similarly, by following the procedures of Parts A–G above, and substituting in for 2-chloropropane in Part A the following compounds:

1-chloroethane;
chloromethane;
2-chlorobutane, there are obtained the corresponding compounds where $R^3$ is, respectively, ethyl, methyl and butyl, such as:

1-diphenylmethyl-4-[1-(2-phenyl-5-methyl-1H-imidazol-4-yl)propyl]piperazine trihydrochloride;

1-diphenylmethyl-4-[1-(2-phenyl-5-methyl-1H-imidazol-4-yl)ethyl]piperazine trihydrochloride;

1-diphenylmethyl-4-[1-(2-phenyl-5-methyl-1H-imidazol-4-yl)-2-methylbutyl]piperazine trihydrochloride;

1-(4,4-diphenylbutyl)-4-[1-(2-phenyl-5-methyl-1H-imidazol-4-yl)-2-methylbutyl]piperazine trihydrochloride;

1-[1-(4-chlorophenyl)-1-(phenyl)methyl]-4-[1-(2-phenyl-5-methyl-1H-imidazol-4-yl)propyl]piperazine trihydrochloride;

1-diphenylmethyl-4-[1-(2-(4-methylphenyl)-5-ethyl-1H-imidazol-4-yl)propyl]piperazine trihydrochloride; and 1-diphenylmethyl-4-[1-(2,5-diphenyl-1H-imidazol-4-yl)-2-methylbutyl]piperazine trihydrochloride.

4I. Formula A Varying m

Similarly, by following the procedures of Parts A–H above, but replacing the piperazines there-used with the corresponding diazepines, the compounds of Formula A wherein m is 3 are obtained.

EXAMPLES 5–11

The following examples illustrate the preparation of representative pharmaceutical formulations containing an active compound of Formula A, e.g., 1-diphenylmethyl-4-[(2-(4-methylphenyl)-5-methylimidazol-4-yl)methyl]-piperazine trihydrochloride. Other compounds and salts of Formula A, such as those prepared in accordance with Examples 1–4, can be used as the active compound in the formulations of Examples 5–11.

EXAMPLE 5

| I.V. Formulation | |
| --- | --- |
| Active compound | 0.14 g |
| Propylene glycol | 20.0 g |
| POLYETHYLENE GLYCOL 400 | 20.0 g |
| TWEEN 80 | 1.0 g |
| 0.9% Saline solution | 100.0 ml |

Other compounds of Formula A and the pharmaceutically acceptable salts thereof may be substituted therein.

EXAMPLE 6

| Ingredients | Quantity per tablet, mgs. |
| --- | --- |
| Active compound | 25 |
| cornstarch | 20 |
| lactose, spray-dried | 153 |
| magnesium stearate | 2 |

The above ingredients are thoroughly mixed and pressed into single scored tablets.

EXAMPLE 7

| Ingredients | Quantity per capsule, mgs. |
| --- | --- |
| Active compound | 100 |
| lactose, spray-dried | 148 |
| magnesium stearate | 2 |

The above ingredients are mixed and introduced into a hard-shell gelatin capsule.

EXAMPLE 8

| Ingredients | Quantity per tablet, mgs. |
| --- | --- |
| Active compound | 1 |
| cornstarch | 50 |
| lactose | 145 |
| magnesium stearate | 5 |

The above ingredients are mixed intimately and pressed into single scored tablets.

EXAMPLE 9

| Ingredients | Quantity per capsule, mgs. |
| --- | --- |
| Active compound | 150 |
| lactose | 92 |

The above ingredients are mixed and introduced into a hard-shell gelatin capsule.

EXAMPLE 10

An injectable preparation buffered to a pH of 7 is prepared having the following composition:

| Ingredients | |
| --- | --- |
| Active compound | 0.2 g |
| KH$_2$PO$_4$ buffer (0.4M solution) | 2 ml |

-continued

| Ingredients | |
|---|---|
| KOH (1N) | q.s. to pH 7 |
| water (distilled, sterile) | q.s. to 20 ml |

EXAMPLE 11

An oral suspension is prepared having the following composition:

| Ingredients | |
|---|---|
| Active compound | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the structure represented by the formula:

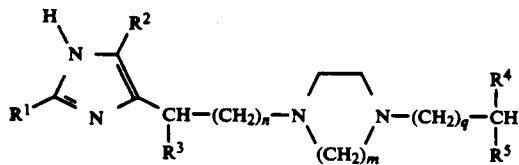

wherein:
$R^1$ is aryl, lower alkyl, cycloalkyl or hydrogen;
$R^2$ is aryl, lower alkyl or hydrogen;
$R^3$ is lower alkyl, hydroxy, or hydrogen;
$R^4$ is aryl or hydrogen;
$R^5$ is aryl or hydrogen;
m is three;
n is zero, one or two, provided that when $R^3$ is hydroxy, n is one or two; and
q is zero, one, two, or three;
or a pharmaceutically acceptable salts thereof.

2. The compound of claim 1 wherein $R^1$ is aryl.
3. The compound of claim 2 wherein q is zero, and n is zero.
4. The compound of claim 3 wherein $R^2$ is methyl.
5. The compound of claim 4 wherein $R^4$ is the same as $R^5$.
6. The compound of claim 5 wherein $R^3$ is hydrogen.
7. The compound of claim 6 wherein $R^4$ and $R^5$ are phenyl.
8. The compound of claim 1 wherein m is three, q is zero, n is zero, $R^1$ is phenyl, $R^2$ is methyl, $R^3$ is hydrogen, and $R^4$ and $R^5$ are phenyl.
9. The compound of claim 1 wherein said pharmaceutically acceptable salt is the trihydrochloride.
10. A pharmaceutical formulation comprising a compound of claim 1 and a pharmaceutically acceptable excipient.
11. A compound having the structure represented by the formula:

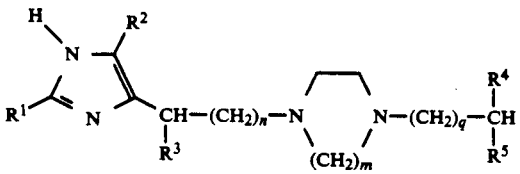

wherein:
$R^1$ is aryl, lower alkyl, cycloalkyl or hydrogen, except that when $R^3$ is lower alkyl or hydrogen, $R^1$ is aryl or cycloalkyl;
$R^2$ is aryl, lower alkyl or hydrogen;
$R^3$ is lower alkyl, hydroxy, or hydrogen;
$R^4$ is aryl or hydrogen;
$R^5$ is aryl or hydrogen;
m is or three;
n is zero, one or two, provided that when $R^3$ is hydroxy, n is one or two; and
q is zero, one, two, or three;
or a pharmaceutically acceptable salts thereof.

12. The compound of claim 11 wherein $R^1$ is aryl or cycloalkyl.
13. A pharmaceutical formulation comprising a compound of claim 11 and a pharmaceutically acceptable excipient.

* * * * *